United States Patent
Pickrell et al.

(10) Patent No.: US 11,124,831 B2
(45) Date of Patent: Sep. 21, 2021

(54) ULTRA-LOW COVERAGE GENOME SEQUENCING AND USES THEREOF

(71) Applicant: New York Genome Center, Inc., New York, NY (US)

(72) Inventors: Joseph K. Pickrell, New York, NY (US); Tomaz Berisa, New York, NY (US); Suma Jaini, New York, NY (US); Brian Houck-Loomis, New York, NY (US); Kaja Wasik, New York, NY (US)

(73) Assignee: NEW YORK GENOME CENTER, New York, NY (US)

( * ) Notice: Subject to any disclaimer, the term of this patent is extended or adjusted under 35 U.S.C. 154(b) by 863 days.

(21) Appl. No.: 15/673,753

(22) Filed: Aug. 10, 2017

(65) Prior Publication Data

US 2018/0044730 A1 Feb. 15, 2018

Related U.S. Application Data

(60) Provisional application No. 62/373,054, filed on Aug. 10, 2016.

(51) Int. Cl.
*C12Q 1/6874* (2018.01)
*G16B 10/00* (2019.01)
(Continued)

(52) U.S. Cl.
CPC ......... *C12Q 1/6874* (2013.01); *C12Q 1/6869* (2013.01); *G16B 10/00* (2019.02);
(Continued)

(58) Field of Classification Search
CPC ............ C12Q 2535/122; C12Q 1/6869; C12Q 1/6809; C12Q 1/6827; C12Q 2600/156;
(Continued)

(56) References Cited

U.S. PATENT DOCUMENTS 10,095,831 B2 * 10/2018 Duenwald .............. G16B 30/00
2013/0073217 A1 3/2013 Dewey et al.
(Continued)

FOREIGN PATENT DOCUMENTS

| WO | 2015/126904 A1 | 8/2015 |
| WO | 2015/195816 A1 | 12/2015 |
| WO | 2016/061260 A1 | 4/2016 |

OTHER PUBLICATIONS

Pollen et al. Low-coverage single cell mRNA sequencing reveals cellular heterogeneity and activated signaling pathways in developing cerebral cortex. Published online Aug. 3, 2014, Nature Biotechnology, vol. 32, No. 10 pp. 1053-1058, plus two pages of online methods.*
(Continued)

*Primary Examiner* — Mary K Zeman
(74) *Attorney, Agent, or Firm* — Wolter VanDyke Davis, PLLC; Eugene J. Molinelli

(57) ABSTRACT

Methods are provided for analyzing one or more genetic samples, comprising procuring one or more genetic samples comprising genetic material from one or more individuals and sequencing the genetic material using non-targeted, ultra-low coverage sequencing to obtain genetic information for individual associated with the one or more genetic samples. Personal and genetic information associated with the individuals is stored in a database for retrieval and manipulation.

17 Claims, 18 Drawing Sheets

(51) Int. Cl.
| | |
|---|---|
| G16B 20/00 | (2019.01) |
| G16B 30/00 | (2019.01) |
| C12Q 1/6869 | (2018.01) |
| G16B 20/20 | (2019.01) |
| G16B 30/10 | (2019.01) |

(52) U.S. Cl.
CPC ............. *G16B 20/00* (2019.02); *G16B 20/20* (2019.02); *G16B 30/00* (2019.02); *G16B 30/10* (2019.02)

(58) Field of Classification Search
CPC ................ C12Q 1/6883; C12Q 1/6851; C12Q 2537/165; C12Q 2600/112; C12Q 1/06; C12Q 2537/16; C12Q 1/6806; C12Q 2563/179; C12Q 2537/159; G16B 30/00; G16B 30/10; G16B 20/00; G16B 20/20; G16B 40/00; G16B 30/20; G16B 20/10; G16B 50/00; G16B 45/00; G16B 25/00; G16B 40/20; G16B 5/00; G16B 35/00; G16B 40/10; G16B 40/30; G16B 50/30; G16B 10/00; G16B 20/30; G16B 25/20; G16B 35/10; G16B 50/10; G16B 99/00; G16H 10/40; G16H 50/20; G16H 50/70; G16H 10/60; G16H 50/30; G16H 50/50; G16H 70/00; G16H 80/00; G06F 17/18; G06F 19/00; G06F 16/245; G06F 19/18; G06F 19/22; G06F 16/9038; G01N 2800/52; G01N 2800/50; G06N 20/00; G06N 3/08; G06N 5/003; G06N 5/04; G06N 20/10; G06N 3/02; G06N 3/0445; G06N 7/005; G06N 3/088; Y02A 90/26; G06K 9/6218; G06K 9/6297; G06K 9/6256; G06K 9/6267; C12N 15/1093; C12N 15/1065; C40B 40/06; C40B 30/00; C40B 40/08; C40B 20/06; G16C 20/70

See application file for complete search history.

(56) References Cited

U.S. PATENT DOCUMENTS

| | | | | |
|---|---|---|---|---|
| 2014/0067280 | A1* | 3/2014 | Vockley | G16B 30/00 702/20 |
| 2014/0200147 | A1* | 7/2014 | Bartha | G16B 20/00 506/2 |
| 2015/0066824 | A1 | 3/2015 | Harris | |
| 2015/0247184 | A1 | 9/2015 | Vermeesch et al. | |
| 2016/0238484 | A1* | 8/2016 | Veyrat-Masson | B64D 37/02 |
| 2016/0281166 | A1* | 9/2016 | Bhattacharjee | C12Q 1/6883 |
| 2017/0132360 | A1* | 5/2017 | Green | G16B 30/00 |
| 2017/0228496 | A1* | 8/2017 | Boutros | C12Q 1/6886 |
| 2019/0177786 | A1* | 6/2019 | Kocher | C12Q 1/6869 |
| 2019/0252042 | A1* | 8/2019 | Mahe | C12Q 1/689 |

OTHER PUBLICATIONS

Davies et al. Rapid genotypeimputation from sequence without reference panels. Nature Genetics vol. 48 No. 8 pp. 965-969 published online Jul. 4, 2016.*

Nicod et al. Genome-wide association of multiple complex traits in outbred mice by ultra-low coverage sequencing. Nature Genetics , vol. 48 No. 8 pp. 912-917, published online Jul. 4, 2016.*

Yu et al. Comparing a few SNP calling algorithms using low-coverage sequencing data. BMC Bioinformatics vol. 14:274 15 pages. published in 2013.*

Klein et al. LOCAS—a low coverage assembly tool for resequencing projects. PLosOne vol. 6 issue 8 e23455, published Aug. 2011.*

Pollen et al. Low-coverage single cell mRNA sequencing reveals cellular heterogeneity and activated signaling pathways in developing cerebral cortex. Published online Aug. 3, 2014, Nature Biotechnology, vol. 32, No. 10 pp. 1053-1058, plus two pages of online methods, included. (Year: 2014).*

Nicod et al. Genome-wide association of multiple complex traits in outbred mice by ultra-low-coverage sequencing. Nature Genetics (published online Jul. 4, 2016) vol. 48, No. 8, p. 912-922 plus supplemental information. (Year: 2016).*

European Search Report issued in EP application 17840256.6, dated Mar. 4, 2020, pp. 1-14.

Sims et al., Sequencing depth and coverage: Key considerations in genomic analyses, Nature Review Genetics, 2014 pp. 121-132, vol. 15.

Zhi et al., Genotype calling from next generation sequencing data using Haplotype information of reads, Bioinformatics, 2012, pp. 938-946, vol. 28.

ISA/US: International Patent Application No. PCT/US2017/046238, International Search Report and Written Opinion, dated Oct. 24, 2017, 14 pages.

Adey, A., et al., (2010) "Rapid, low-input, low-bias construction of shotgun fragment libraries by high-density in vitro transposition," Genome Biology, 11:R119, 11-17.

Baym, M. et al., (2015) "Inexpensive multiplexed library preparation for megabase-sized genomes," PLOSOne, 2015, 10(5).

Browning, B., et al., (2009) "Simultaneous genotype calling and haplotype phasing improves genotype accuracy and reduces false-positive associations for genome-wide association studies," American Journal of Human Genetics, 35(6):847-61.

Cai et al. (2015) "Sparse whole-genome sequencing identifies two loci for major depressive disorder," Nature, 523, 588-591.

DeAngelis, M. et al. (1995) "Solid-phase reversible immobilization for the isolation of the PCR products," Nucleic Acid Research, 23:22, 4742-4743.

Kent, W. James, et al., (2002) "The human genome browser at UCSC," Genome Research,12(6):996-1006. Published online before print in May 2002 at http://www.genome.org/cgi/doi/10.1101/gr.229102.

Pasaniuc, B. et al. (2012), "Extremely low-coverage sequencing and imputation increases power for genome-wide association studies," Nature Genetics, 44(6), 631-635.

Picelli, S., et al. (2014), "Tn5 transposase and tagmentation procedures for massively scaled sequencing projects," Genome Research, 2016, 24:2033-2040. Published online before print on Jul. 30, 2014 at http://www.genome.org/cgi/doi/10.1101/gr.177881.114 0.

Price, A., et al. (2006), "Principal components analysis corrects for stratification in genome-wide association studies," Nature Genetics 38(8):904-909.

Pritchard, J. k., et al. (2000), "Inference of population structure using multilocus genotype data," Genetics,155(2): 945-959.

Sullivan, P. (2015), "Genetics of disease: Associations with depression," Nature, 523, 539-540.

Skoglund, P. (2012), "Origins and Genetic Legacy of Neolithic Farmers and Hunter-Gatherers in Europe," Science, 336 (6080):466-469.

Wang, C., et al. (2014), "Ancestry estimation and control of population stratification for sequence-based association studies," Nature Genetics, 46(4), 409-415.

Wood D. et al. (2014), "Kraken: ultrafast metagenomic sequence classification using exact alignments," Genome Biology, 15:R46, 1-12, http://genomebiology.com/2014/15/3/R46.

* cited by examiner

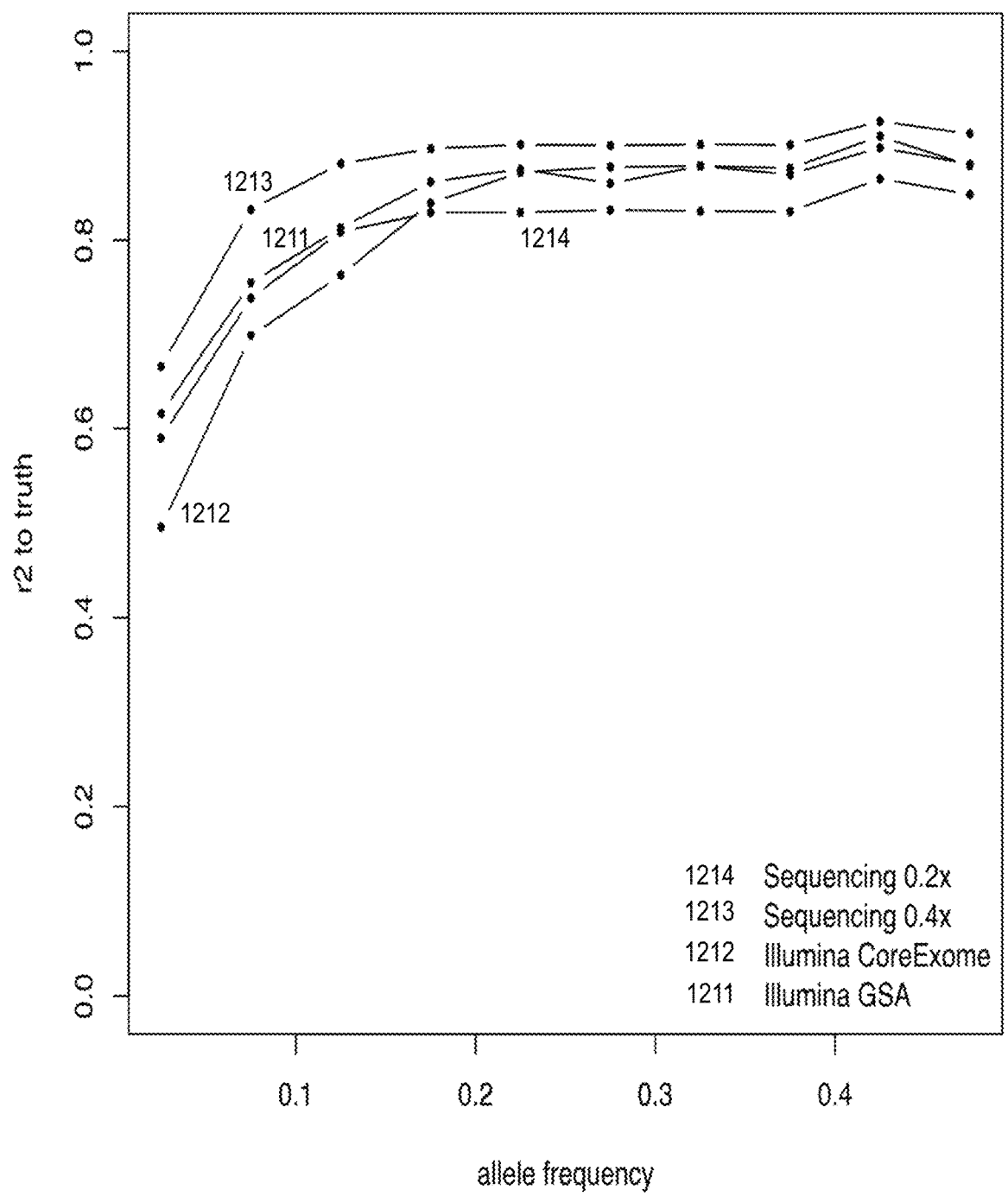

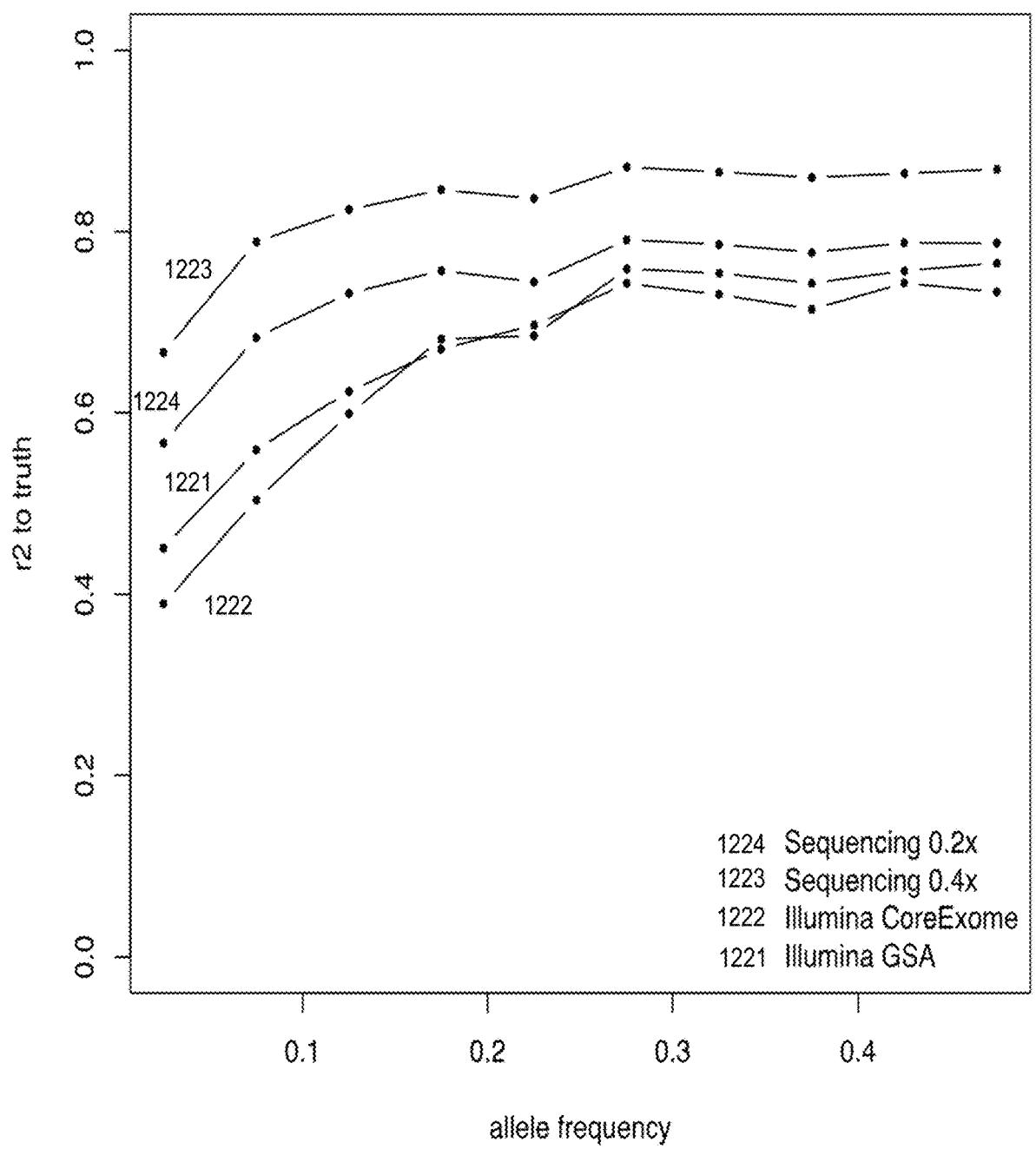

ULTRA-LOW COVERAGE GENOME SEQUENCING AND USES THEREOF

CROSS-REFERENCE TO RELATED APPLICATIONS

This application claims benefit of Provisional Appln. 62/373,054, filed Aug. 10, 2016, the entire contents of which are hereby incorporated by reference as if fully set forth herein, under 35 U.S.C. § 119(e).

TECHNICAL FIELD

Embodiments of the disclosure relate generally to improving methods and automatic processors for obtaining and analyzing genetic and phenotypic information.

BACKGROUND

Commercial services that provide an analysis of an individual's genome for a fee are becoming increasingly popular. The information obtained by such analyses can relate to many different aspects of an individual's background or genetic makeup which might be of interest, including ancestry, familial relationships, the presence of genetic markers for disease, and cryptic physical or behavioral traits that the individual has or is at risk for developing.

Current commercial technology used by the major direct-to-consumer genomics analysis companies (e.g., 23andMe, AncestryDNA, and FamilyTreeDNA) for obtaining genome-wide genetic information involve a genotyping microarray. In this technology, DNA is extracted from an individual (usually from saliva or blood), digested, and hybridized to a chip or other solid support on which a set of DNA probes has been immobilized. These probes represent a predetermined subset of all sites in a given genome (for example, single nucleotide polymorphisms) known to vary across individuals. A typical genotyping microarray can assay around 500,000-1.5M known sites of genetic variation. Although genotyping by microarray is currently the most inexpensive genotyping technology used by direct-to-consumer genomics analysis companies, each sample analyzed can cost the consumer up to several hundred dollars.

The cost of nucleic acid sequencing appears to be declining faster than the cost of microarray genotyping, and thus sequencing-based genotyping techniques may soon be more economically viable. However, current sequencing-based genotyping techniques are cumbersome or time-consuming, are not sufficiently reliable and/or do not provide accurate enough results to satisfy the commercial market.

A typical sequencing-based genotyping technique uses "high coverage" sequencing (e.g., 30× average coverage), meaning that each base of the genome is covered on average by 30 sequencing reads. Such a technique requires considerable time and effort, however, and will likely not be commercially viable even with declining sequencing costs. The cost per sample for sequencing-based genotyping can be lowered by using "low-coverage" genome sequencing; e.g., greater than about 1× to about 10× average coverage, or "extremely low" or "ultra-low coverage" genome sequencing, which has been defined as anything about 1× or less average genome coverage. But as mentioned above, cost, reliability and accuracy tradeoffs make even the current low or ultra-low coverage sequencing genotyping techniques prohibitive in a commercial setting as well as in many research settings.

For example, in one study, low-coverage sequencing (on average 1.6× genome coverage) was used to identify genetic variants associated with major depressive disorder (CONVERGE consortium, 2015, Sparse whole-genome sequencing identifies two loci for major depressive disorder, Nature 523, 588-591). This approach was received with skepticism, however, because of the relatively high error rates observed; approximately 2% of the genetic variants identified in the CONVERGE study could not be replicated with a different method; whereas, in contrast, only about less than 0.5% of genetic variants identified with a genotyping array could not be replicated (Sullivan P, 2015, Genetics of disease: Associations with depression, Nature 523, 539-540). The author, one of the leading psychiatric geneticists in the world, included a statement indicating a preference for the microarray approach over the low coverage of 1.6× or less. Specifically, because of the high error rates, the author teaches, "To my knowledge, this is the only published study in which genotyping involved low-coverage sequencing of the whole genome. Because of decreases in the costs of genotyping arrays, it may be one of the last."

Others have used ultra-low coverage sequencing in genotyping studies, but this was done more out of necessity than from any particular advantage to the sequencing technique. See, e.g., Skoglund et al. (2012), Origins and genetic legacy of Neolithic farmers and hunter-gatherers in Europe, Science 336, 466-469, who used ultra-low coverage sequencing to analyze ancient human DNA samples. Here, the ultra-low coverage was a function of not having sufficient DNA in the samples to sequence, rather than being used as a cost- and time-saving measure. Because of the extremely poor quality of ancient DNA samples—for example, only a fraction of the ancient individual's genome is present, and what is present is typically degraded—analysis of ancient DNA is subject to extremely high error rates. Often, such samples must undergo multiple sequencing runs, and/or the results subjected to significant manipulation and statistical analysis, in order to produce meaningful data.

Another study evaluated the use of "off target" reads from the targeted sequencing of specific genomic sites in sequence-based association studies, to infer individual genotypes (Wang et al., Ancestry estimation and control of population stratification for sequence-based association studies, Nature Genetics 46(4), 409-415). The targeted sequencing coverage was approximately 10×, while the incidental, "off target" coverage was >0.1×. Because the targeted genomic regions in this type of sequencing technique are typically short and do not represent a significant fraction of the genome, the targeted regions do not contain enough genetic information to estimate ancestry relationships between individuals. Wang et al. thus used simulated sequencing data from off-target areas to infer ancestry and factor out spurious association signals due to ancestral relatedness of samples. Using their data simulations, Wang et al. were able to identify population stratification of samples within a continental region such as Europe, but suggested that multiple sequencing runs (e.g., over ten) were desirable to increase accuracy. Moreover, their technique could only identify individual ancestry relative to a reference panel and would not reveal cryptic relatedness between samples from two individuals. The Wang et al. technique also examined only one sample at a time, and thus is not suited for high-throughput screenings.

Pasaniuc et al. (2012) suggested that that the imperfect or incomplete genotypes obtained from ultra-low coverage sequencing could be "filled in" with a statistical technique called genotype imputation, and demonstrated this technique using simulated sequencing data or by post-hoc analyses of actual sequencing data (Pasaniuc et al., Extremely low-coverage sequencing and imputation increases power for genome-wide association studies, Nature Genetics 44(6), 631-635). Although the imputation technique could identify common genetic variants and (less reliably) lower-frequency variants, the technique could not identify rare genetic disease variants.

SUMMARY

It was decided that there is a need for an efficient, low-cost, reliable and accurate sequencing-based genotyping technique for use in research and commercial settings, which can identify rare disease variants, elucidate cryptic relatedness among genetic samples and generate other useful genetic and phenotypic information from individual genetic samples.

Thus in a first set of embodiments, a method for analyzing one or more genetic samples, comprises the following steps: One or more genetic samples comprising genetic material are procured from one or more individuals having a genotype, and each genetic sample is correlated with the individual from which is was procured. The genetic material from each of the one or more genetic samples was sequenced using non-targeted, ultra-low coverage sequencing to determine a plurality of genetic reads for each of the one or more genetic samples. The ultra-low coverage is determined with reference to a target genome, and the genetic material is substantially non-ancient genetic material. The plurality of genetic reads obtained by sequencing each of the one or more genetic samples is aligned to one or more reference genomes, which can be the same as or different from the target genome, to produce a plurality of aligned genetic reads for each of the one or more genetic samples. The one or more genetic samples is assigned to one or more genotypic or phenotypic groups or the presence of one or more allelic variants is determined, based on the aligned genetic reads and without imputing the genotype of the one or more genetic samples with respect to the one or more reference genomes, using a processor configured to produce competitive results in less time and fewer computational resources than conventional methods.

In a second set of embodiments, a method for analyzing one or more genetic samples, comprises the following steps: A plurality of genetic samples comprising genetic material is procured from one or more individuals having a genotype, and each genetic sample is correlated with the individual from which is was procured. The genetic material from each of the plurality of genetic samples is sequenced using non-targeted, ultra-low coverage sequencing to determine a plurality of genetic reads for each of the plurality of genetic samples. The ultra-low coverage is determined with reference to a target genome, and the genetic material is substantially non-ancient genetic material. The plurality of genetic reads obtained by sequencing each of the plurality of genetic samples is aligned to one or more reference genomes to produce a plurality of aligned genetic reads for each of the plurality of genetic samples, and a sample pool is created by combining the plurality of aligned genetic reads from all or a subset of the plurality of genetic samples. An imputed genotype of the individual or individuals associated with the sample pool is obtained by calculating the degree of similarity of the pooled aligned genetic reads to a reference dataset; and the individual is assigned to a genotypic or phenotypic group based on assignment of at least one or more rare allelic variants to the imputed genotype using a processor configured to produce competitive results in less time and fewer computational resources than conventional methods.

In a third set of embodiments, a method is provided for identifying cryptic ancestral relatedness between at least two genetic samples. This method comprises the following steps: At least a first genetic sample is procured from a first individual having a first genotype and a second genetic sample is procured from a second individual having a second genotype. The genetic material from the first and second genetic samples is sequenced using non-targeted, ultra-low coverage sequencing to generate a plurality of first genetic reads for the first genetic sample and a plurality of second genetic reads from the second genetic sample. The ultra-low coverage is determined with reference to a target genome, and the genetic material is substantially non-ancient genetic material. The plurality of first genetic reads and the plurality of second genetic reads are aligned to one or more reference genomes to produce a plurality of first aligned genetic reads and a plurality of second aligned genetic reads. The first and second aligned genetic reads are used to identify a set of rare genetic variants in each of the first and second individuals by comparing the set of rare genetic variants identified in the first and second individuals to produce a fraction of matching rare genetic variants between the first and second individuals. The produced fraction of matching rare genetic variants is used to determine the degree of genetic relatedness between the first and second individuals to within a predetermined number of generations, without imputing the genotype of the one or more genetic samples with respect to the one or more reference genomes using a processor configured to produce competitive results in less time and fewer computational resources than conventional methods.

In a fourth set of embodiments, a method is provided for creating a database of storable, retrievable and manipulatable genotypic and phenotypic information. This method comprises the following steps: One or more genetic samples comprising genetic material is procured from one or more individuals having a genotype. The genetic material from each of the one or more genetic samples is sequenced using non-targeted, ultra-low coverage sequencing to determine a plurality of genetic reads for each of the one or more genetic samples. The ultra-low coverage is determined with reference to a target genome, and the genetic material is substantially non-ancient genetic material. The plurality of genetic reads obtained by sequencing each of the one or more genetic samples is aligned to one or more reference genomes to produce plurality of aligned genetic reads for each of the one or more genetic samples to produce genetic information corresponding to each of the one or more genetic samples, without imputing the genotype of the one or more genetic samples with respect to the one or more reference genomes. The information for each of the one or more genetic samples is correlated with personal information, if any, provided by or on behalf of the individual corresponding to the genetic sample; and the one or more genetic samples or individuals is assigned to one or more genotypic or phenotypic groups with associated probability based on the genetic and personal information corresponding to that genetic sample or individual. The information thus obtained comprising the database is stored in a manner in which it can be retrieved and manipulated.

In a fifth set of embodiments, a database comprises fields for storing data that indicates personal and genetic information derived from a plurality of individuals each having a genotype, wherein the genetic information is derived from a plurality of genetic samples provided by the plurality of individuals. Each genetic sample corresponds to a different individual, and the genetic information is derived by the following steps: One or more genetic samples comprising genetic material is procured from one or more individuals having a genotype, and the genetic material from each of the one or more genetic samples is sequenced using non-targeted, ultra-low coverage sequencing to determine a plurality of genetic reads for each of the one or more genetic samples. The ultra-low coverage is determined with reference to a target genome, and the genetic material is substantially non-ancient genetic material. The plurality of genetic reads obtained by sequencing each of the one or more genetic samples is aligned to one or more reference genomes to produce plurality of aligned genetic reads for each of the one or more genetic samples. This plurality of aligned genetic reads produces genetic information corresponding to each of the one or more genetic samples, without imputing the genotype of the one or more genetic samples with respect to the one or more reference genomes. The information for each of the one or more genetic samples is correlated with personal information, if any, provided by or on behalf of the individual corresponding to the genetic sample; and the personal and genetic information comprising the database is stored in a manner in which it can be retrieved and manipulated.

BRIEF DESCRIPTION OF THE FIGURES

Embodiments are illustrated by way of example, and not by way of limitation, in the figures of the accompanying drawings in which like reference numerals refer to similar FIG. 1A through FIG. 1C are block diagrams that illustrate relative abundance of reference sequences in a sample;

FIG. 12A and FIG. 12B are graphs that illustrate example surprising good performance using the methods described herein compared to conventional and more costly methods, according to various embodiments;

DETAILED DESCRIPTION

Figure 1A:
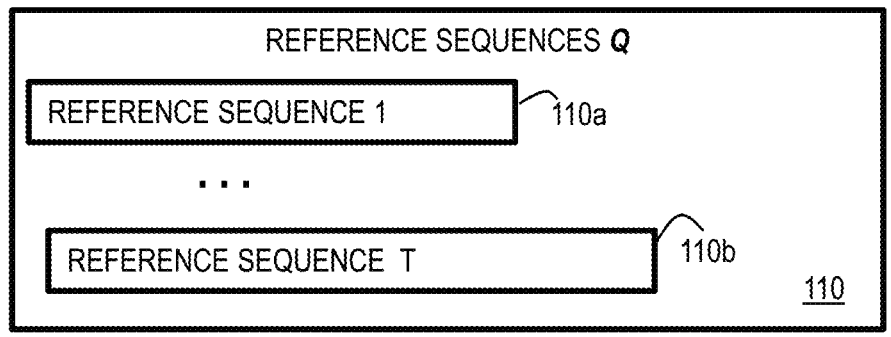
FIG. 1D is a block diagram that illustrates an example process to obtain reads from a sample and associate reads with reference sequences, according to an embodiment.

The following detailed description is explanatory and is intended to provide further explanation of the present disclosure described herein. Other advantages and novel features will be readily apparent to those skilled in the art from the following detailed description of the present disclosure.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of determining ancestry and oral biome from ultra low coverage sequencing of biological samples from individuals using known reference genomes and haplotype panels and user input. However, the invention is not limited to this context. In other embodiments other characteristics of individuals are determined from ultra low coverage sequencing of samples from individuals or groups of individuals with or without known reference genomes or panels.

Deoxyribonucleic acid (DNA) is a, usually double-stranded, long molecule that is used by biological cells to encode other shorter molecules, such as proteins, used to build and control all living organisms. DNA is composed of repeating chemical units known as "nucleotides" or "bases." There are four bases: adenine, thymine, cytosine, and guanine, represented by the letters A, T, C and G, respectively. Adenine on one strand of DNA always binds to thymine on the other strand of DNA; and guanine on one strand always binds to cytosine on the other strand and such bonds are called base pairs. Any order of A, T, C and G is allowed on one strand, and that order determines the reverse complementary order on the other strand. The actual order determines the function of that portion of the DNA molecule. Information on a portion of one strand of DNA can be captured by ribonucleic acid (RNA) that is also composed of a chain of nucleotides in which uracil (U) replaces thymine (T). Determining the order, or sequence, of bases on one strand of DNA or RNA is called sequencing. A portion of length k bases of a strand is called a k-mer; and specific short k-mers are called oligonucleotides or oligomers or "oligos" for short. The base found at one location (locus) on the strand is called the value at that locus.

Figure 1B:
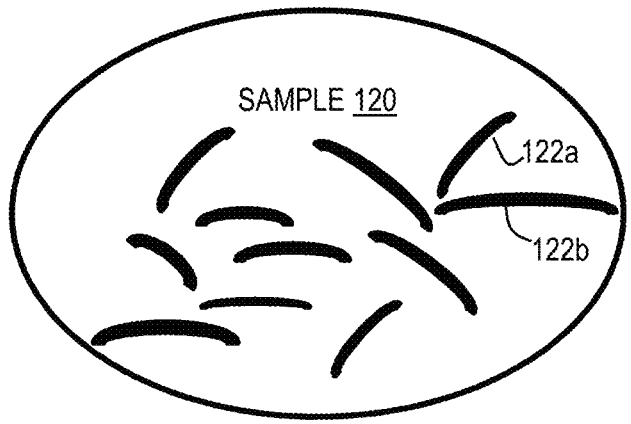
Figure 1C:
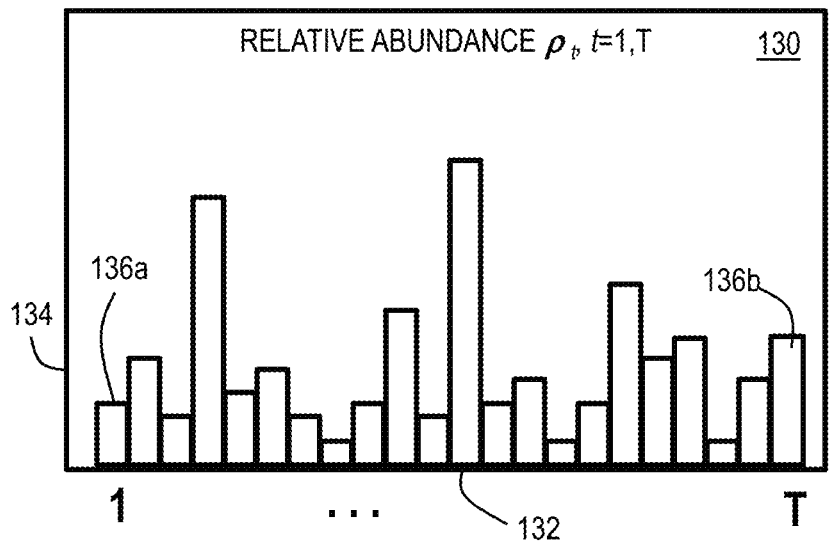

FIG. 1A through FIG. 1C are block diagrams that illustrate relative abundance of reference sequences in a sample. FIG. 1A is a block diagram that illustrates an example data structure 110 of C reference sequences Q, including field 110a holding data that indicates first reference sequence ($Q_1$), through field 110b holding the last (Tth) reference sequence ($Q_T$), among others indicated by ellipsis. An individual reference sequence is indicated by Qt, where $t \in \{1, \ldots, T\}$. A reference sequence can refer to a normal (also called most common or consensus sequence or baseline or disease free sequence) or a SNP, CNV, PAV or other known structural variation of the normal sequence. The reference sequence can be an entire genome of a subject or population of subjects, or one or more chromosomes of the genome, such as a reference panel for a particular haplotype, or one or more regions of interest, such as sequences of a fixed size on one or more chromosomes, including all contiguous bases or excluding one or more bases at particular locations, as specified by a mask of locations of no interest. The term bin will refer to each of one or more such regions of interest, in some embodiments excluding bases specified in such a mask, if any.

FIG. 1B is a block diagram that represents an example sample 120 with multiple occurrences of nucleic acids, e.g., 122a, 122b (collectively referenced hereinafter as nucleic acids 122) each having at least one of the reference sequences or a fragment thereof (e.g., in the case of extracellular DNA in the blood or saliva of a subject from tumors or fetal cells or food or oral biome). There may be several occurrences of a nucleic acid with one of the reference sequences and few or no occurrences of nucleic acids with another of the reference sequences. FIG. 1C is a bar graph 130 that illustrates example relative abundance data. The horizontal axis 132 indicates the reference sequences $Q_t$ $\{t=1, T\}$. The vertical axis 134 indicates relative number of nucleic acids in the sample (designated by the symbol ρ) with each reference, with a higher value indicating a greater abundance of the associated reference sequence. Graph 130 indicates that $Q_1$ occurs in the sample 120 with a relative abundance $\rho_1$ indicated by bar 136a, and $Q_T$ occurs in the sample 120 with a relative abundance $\rho_{TT}$ indicated by bar 136b. The abundance distribution is represented by $\rho=\rho_t$, $\{t=1,T\}$.

A problem is that ρ is not measured directly during sequencing experiments, but must be inferred by a large number S of sequencing reads (simply called reads, herein), represented by the symbol $q_s$ $\{s=1, S\}$, where each sequence of each read is short compared to a reference sequence $Q_t$. To ensure reliability of the relative abundance, high coverage is desirable for each reference sequence or portion thereof, e.g., converge is 10× or 100× or more for each reference sequence in conventional methods.

Figure 1D:
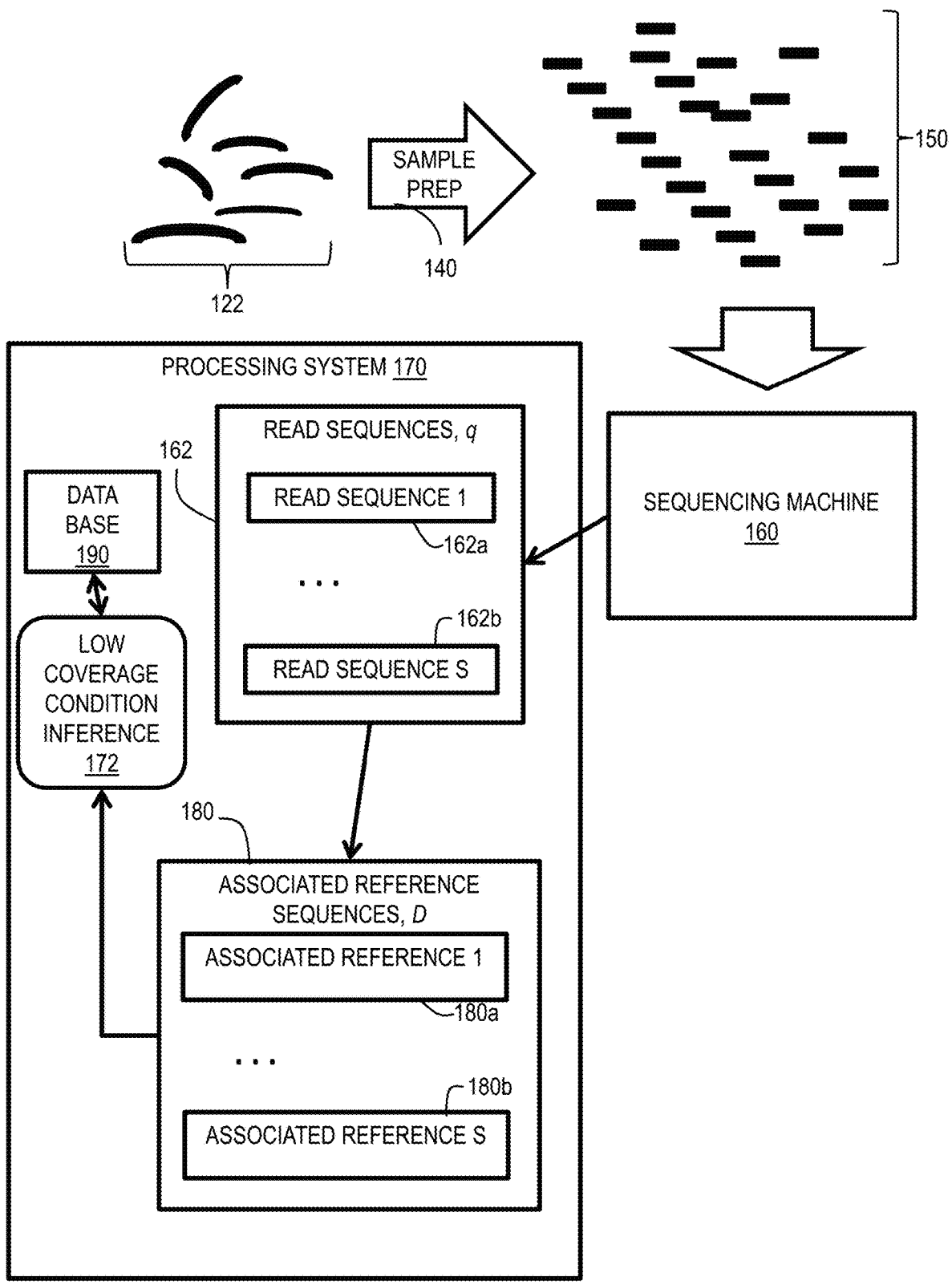

FIG. 1D is a block diagram that illustrates an example process to obtain reads from a sample and associate reads with reference sequences, according to an embodiment. The nucleic acids 122 in a sample are prepared for the sequencer in a wide variety of ways known in the art, often by de-naturing to release the nucleic acids, fragmentation to allow the short reads to begin sequencing from anywhere within the nucleic acid having the reference sequence, to hybridization or replication or amplification or size selection, among others, or some combination, which collectively are referenced herein as sample preparation process 140. The resulting short nucleic acids 150 are then sequenced with whatever bias or systematic variation are introduced by the sequencing process in sequencing machine 160. The reads $q_s$ $\{s=1, S\}$ are recorded in a data structure 162 with a field holding data that represents each read sequence, such as field 162a for $q_1$ to field 162b for $q_S$, among others indicated by ellipsis.

If each read were uniquely found in one and only one reference sequence, then one of the T reference sequences $Q_t$ can be associated with each read, as indicated by the data structure 180 which associates with each read $q_s$ $\{i \in 1, S\}$ an associated reference sequence $D_s$, with $s \in \{1, \ldots, S\}$ and where $D_s=t$ with $t \in \{1, \ldots, T\}$. In some embodiments, the data structure 180 also indicates the positions within the reference sequence t that are covered by the read, such as positions x to y within the reference sequence t. Thus data structure 180 represents a set of aligned reads, i.e., reads associated with a particular reference sequence or position therein. If a read could be associated with two or more difference reference sequences, then the read is attributed to one of them, or a fraction of the read is attributed to each of two or more of them, or the read is discarded. Then a histogram of the distribution of the $D_s$ among the T references sequences could be used as an approximation of the abundance distribution ρ, or corrected for the known or inferred non-random sampling introduced by processes 140 and machine 160—corrections represented by particular values for a parameters set designated θ. The adjusted abundances are designated $A_t$ and are based on the histogram counts for the associated reference sequences $D_s$ and the corrections represented by values for θ.

Using very low and ultra low coverage, the adjustments abundances $A_t$ cannot currently be deduced reliably; and, thus, a histogram of counts for the associated reference sequences cannot currently be inferred. However, using the methods, processors and databases described herein, important information can still be inferred from the set of aligned reads detected in each of multiple different samples. For example, ancestry, level of relatedness, cryptic relatedness, and phenotype or personal information patterns, or both, can be inferred with surprising accuracy. The accuracy, as demonstrated below, is competitive with microarrays due to the occurrence of off-array matches between samples whose data are stored in the database. In addition, the methods, processors and databases described herein can make possible inference that are better that those from microarrays, including impossible to make with microarrays, because of the off-array matches that can be detected with these described technologies. Furthermore, because the cost of very low and ultra low sequencing is coming down, the costs are also expected to be competitive with microarrays.

Figure 13:
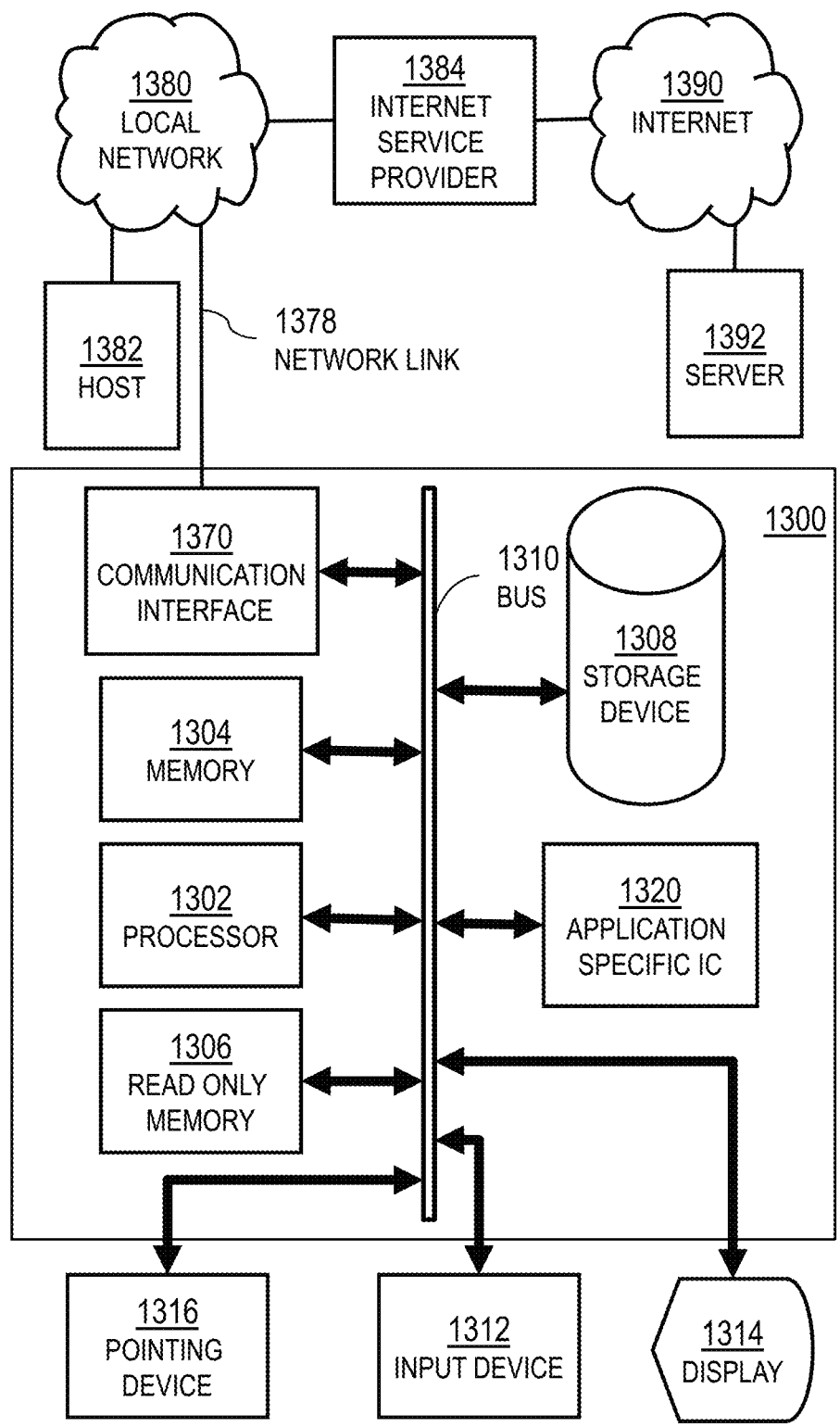
FIG. 13 is a block diagram that illustrates a computer system upon which an embodiment of the invention may be implemented.

In FIG. 1D, the read sequences data structure 162 and associated reference sequences data structure 180 reside on a processing system 170, such as computer system described below with reference to FIG. 13 or one or more chip sets as described below with reference to FIG. 14, or some combination, including components on one or more smart cell phones described below with reference to FIG. 15. The associated reference sequences $D_s$ are stored in a particularly useful way in database 190 and used to infer one or more conditions of one or more subject by low-coverage condition inference module 172 implemented within the processing system 170. Although processes, equipment, and data structures are depicted in FIG. 1A through FIG. 1D as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, in various embodiments, one or both of the data structures 162, 180 or all or part of module 172, or some combination, reside within one or more chip sets in the sequencing machine 160. As another example, input data for one or more fields in the database 190 are provided through a user interface on a software application (App) executing on the smart cell phone depicted in FIG. 15. In another example, the database 190 is on a remote server or distributed among a variety of computer hosts in communication through a network, as depicted in FIG. 13.

Thus the clinical data comprises the S aligned reads of the associated reference sequences D after correction for known systematic errors introduced by the processes 140 and machine 160. Based on the analysis of historical data or other training data, with either baseline (disease free) or known diseased conditions or known other conditions of interest, or some combination, the presence of a disease or other population difference is known to affect the occurrence of aligned reads from different individuals; and, those conditions are inferred by module 172. Module 172 also uses an inferred condition of interest to operate one or more devices, such as presenting data that indicates the condition on a display device, such as display device 1314 in FIG. 13, or dispensing treatment to a subject based on the condition, or cause a treatment to be dispensed or avoided based on the condition inferred.

Conditions of Interest

Every region of a sexually reproduced individual's autosomal genome is represented by a pair of DNA sequences, one inherited from the mother and one from the father. Therefore, for every individual, while most positions (loci) along the genome have the same nucleic acid base and its complement on the opposite strand (value), different loci along the genome can comprise at least two values; for example, a pair of alleles where one value is the variant inherited from the mother and a different value is the variant inherited from the father. Further variation at a given locus can occur through mutation. Genomic loci that comprise at least two values are called polymorphic genetic markers. Individuals, whether produced sexually or asexually, can be characterized with reference to their polymorphic genetic markers, for example, with respect to what markers they possess, or as a function of how many such markers the individual shares with a given population. For example, an individual can be characterized as having a rare disease variant, or can be classified as a member of a particular family or population in which that variant is common. The familial relatedness of two individuals can also be determined by analysis of how similar those individuals' polymorphic genetic markers are. As used herein, an "individual" means any single organism, for example a human or non-human animal, a bacteria, archaea, protist, fungus or plant. In some embodiments, the individual is a human.

A polymorphic genetic marker represents a specific location (locus) on a chromosome which has bee found to have two or more different values. The compilation of multiple polymorphic genetic markers possessed by each individual is referred to as their genotype, which serves as a unique genetic identifier for any given individual. Correlating information about that individual's genotype with their physical characteristics (phenotype), familial relationships or ancestry can help associate specific polymorphic genetic markers with certain physical characteristics or familial/ancestral relationships. The more instances where given polymorphic genetic markers are associated with specific characteristics increases the confidence by which such characteristics can be predicted in, or associated with, other individuals who share those genetic markers. A database that usefully accumulates this information, is therefore a boon to determining phenotype and other personal characteristics based on sequencing data. In order for this database to be filled, individuals are tapped to provide a sample of biologic material, for example blood or saliva, to be analyzed for the presence polymorphic genetic markers. In some embodiments, the individual is also tapped to provide information relating to their physical characteristics and familial or ancestral background, which can then be compared or correlated with the genotypic information derived from analysis of that individual's genetic sample. With enough individuals, as demonstrated herein, the association can be reliably made even using low coverage sequencing.

Thus in one embodiment, a method is provided for analyzing one or more genetic samples using low converge sequencing. The method comprises procuring one or more genetic samples comprising genetic material from one or more individuals. In various embodiments, any suitable technique for obtaining the genetic sample is used, for example by procuring a biological sample that comprises genetic material from the individual. The biological sample comprises sufficient genetic material to allow for subsequent isolation of the genetic material for analysis. In some embodiments, two or more biological samples can be procured from an individual, which can be processed separately or together, and which provide sufficient genetic material for analysis.

As used herein, "genetic material" means any material comprising genetic information, for example DNA (including genomic, mitochondrial, chloroplast, plasmid and cDNA) or RNA (including processed or unprocessed mRNA, tRNA, rRNA and miRNA). In one embodiment, the genetic material comprises DNA. In another embodiment, the genetic material comprises RNA. In a further embodiment, the genetic material comprises genomic DNA.

In various embodiments, such biological samples are procured in any manner suitable for subsequent isolation of genetic material, for example by collecting or drawing a bodily fluid such as blood, lymph, sweat, saliva, urine, tears, synovial fluid, cerebro-spinal fluid, and the like. In various embodiments, the bodily fluid is collected into any suitable container. In some embodiments, the container into which a bodily fluid is collected or drawn contains one or more substances which enhance the preservation of the bodily fluid and/or one or more of its components, and/or which enhances the preservation of any genetic material comprising the bodily fluid, as are well-known to those of ordinary skill in the art.

In one embodiment, the bodily fluid comprising genetic material which is procured from an individual comprises blood. In some embodiments, the blood is collected into a vacuum tube (e.g., Vacutainer, Becton, Dickinson & Co., Franklin Lakes, N.J.), test tube or capillary tube. In various embodiments, the blood is or is not separated into its component parts prior to isolation of genetic material. If the blood is separated into its component parts, genetic material is isolated from the fraction containing nucleated cells (e.g., white blood cells or hematopoietic stem cells). In some embodiments, any collected whole or fractionated blood is stored for later extraction of genetic material, for example under conditions (such as refrigeration or in a stabilizing solution) which would preserve the integrity of the genetic material such that, upon extraction, it could be subject to the methods of the various embodiments. It is also contemplated that, in some embodiments, cells derived from the blood of an individual, for example hematopoietic stem cells, are collected and cultured outside the body for subsequent extraction of genetic material. In some embodiments, collected whole or fractionated blood is packaged and shipped to a facility for subsequent extraction of genetic material. Suitable blood collection techniques, blood collection and storage containers, and blood storage and shipping techniques used in various embodiments, are well-known to those of ordinary skill in the art.

In some embodiments, the bodily fluid comprising genetic material which is procured from an individual comprises saliva. Suitable collection techniques and containers for saliva are well-known to those of ordinary skill in the art, and include, for example, the SS-SAL-1 or SS-SAL-2 saliva DNA collection devices available from SpectrumDNA (Draper, Utah). In some embodiments, saliva is procured from an individual by having the individual spit into the collection device, which, in some embodiments, contains a solution which stabilizes the saliva sample, and inhibits bacterial growth. The saliva collection device is then be packaged and shipped to a facility for subsequent extraction of genetic material from the individual's cells and/or from organisms (such as bacteria) contained within the saliva sample. Other suitable saliva collection techniques, saliva collection and storage containers, and saliva storage and shipping techniques used in various embodiments, are well-known to those of ordinary skill in the art.

In some embodiments, other suitable biological samples for use in the present methods comprise cells or tissue from an individual that are not necessarily derived from bodily fluids. For example, in some embodiments, suitable biological samples comprise epithelial cells, such as those obtained by a swab of bodily surfaces such as the inside of the mouth, nasal passages, vaginal or rectal surfaces, or the skin. In some embodiments, suitable biological samples comprise tissue or non-epithelial cells, such as obtained by a biopsy or by isolating and culturing cells from the individual. Techniques for obtaining, shipping storing and/or culturing tissue or cellular samples from an individual used in various embodiments, are well-known to those of ordinary skill in the art.

In various embodiments, any suitable technique for extracting genetic material from an individual's biological sample can be used in sample prep step 140 depicted above. Such techniques typically employ mechanical, enzymatic and/or chemical means to lyse the cells comprising the biological sample, to free the nucleus and cytoplasm, and then either the nucleus or cytoplasm is subjected to a number of isolation and fractionation steps designed to sequentially and substantially separate the genetic material from the non-genetic material (e.g., cellular debris and other components) of the biological samples. Such techniques also typically employ one or more steps or substances which preserve the integrity of any genetic material e.g., DNA or RNA), for example by inactivating any nucleases which may be present in the biologic sample. As used herein, "substantially separating" genetic material from non-genetic material means that a ratio of genetic material to non-genetic material is such that the non-genetic material does not appreciably interfere with subsequent manipulations of the genetic material, for example amplification and sequencing reactions, normalization of genetic material, or library preparation. Example techniques for substantially separating genetic material from non-genetic material in a biological sample include "salting-out," organic extraction and silica-based extraction methods, and those described in, for example, Green and Sambrook, Molecular Cloning A Laboratory Manual, Volume I, Fourth Edition, Cold Spring Harbor Laboratory Press, 2012. Example techniques for isolating DNA are also shown in the Examples below.

In one embodiment, genetic material is prepared for subsequent sequencing using isolation and recovery techniques and materials comprising a solid support, sometimes referred to herein as a "solid support separation system". Suitable solid support-based techniques and materials for isolation and recovery of genetic material used in various embodiments, are well-known to those of ordinary skill in the art, and include solid phase reversible immobilization ("SPRI") beads having carboxyl groups on the bead surface that reversibly bind nucleic acids in the presence of polyethylene glycol (PEG) and salt. In various embodiments, such beads are magnetic or paramagnetic, so that they can be readily separated from mixtures by applying a magnetic field; see, e.g., Hawkins, et al. Nucleic Acids Res. 1995; 23:22, the entire disclosure of which is herein incorporated by reference. Suitable SPRI bead technology for use in the present methods can be obtained, for example, from Agencourt Bioscience Corp (Beverly, Mass.) as the AMPure® or Orapure™ Solid Phase Reversible Immobilization (SPRI) technology, which are used according to the manufacturer's instructions.

Another suitable solid support-based separation system for preparing genetic material for subsequent sequencing by the present methods in some embodiments involves the CHARGESWITCH® nucleic acid purification technology, available from ThermoFischer Scientific (Waltham, Mass.) and which is described in U.S. Pat. No. 6,914,137, the entire disclosure of which is herein incorporated by reference. The CHARGESWITCH® technology relates to a method for extracting nucleic acids from a biological sample by contacting a biological sample with a solid support material (such as magnetic or non-magnetic beads, membranes, plastic tubes or plates) which have an ionizable coating covalently affixed to the of the solid support. In use, the solid support is contacted with the biologic sample, and the pH lowered such that the coating on the solid support is positively charged and will bind negatively charged nucleic acids, allowing easy removal of proteins and other contaminants.

In one embodiment, genetic material is prepared for sequencing according to the present methods by using "Tunable Electrostatic Capture" or "TEC" solid support separation systems, as described in U.S. patent application Ser. No. 15/097,781 filed on Apr. 13, 2016, the entire disclosure of which is herein incorporated by reference. In general, the TEC solid supports comprise ionizable ligands (such as histamine ligands) covalently attaching to a solid support. The ionizable functionality of the ligand can be partially or fully electrostatically charged, or can be neutral, depending on the pKa of the ionizable functionality and the pH of the medium in which the ionizable functionality is used. The ionizable functionality of the TEC ligands can be adjusted to be positively charged when the pKa of the ionizable functionality is greater than pH of the binding conditions. Conversely, the ionizable functionality of the TEC ligands can be adjusted to be neutrally charged when the pKa of ionizable functionality is less than pH of the desorption or release conditions. In general, the binding and desorption or release conditions for nucleic acids are dictated by the binding or release buffers. As such, the TEC solid supports are used to capture nucleic acids from a biological sample, which then allows for subsequent manipulations such as size separation, concentration normalization and/or sequencing of the nucleic acids. Example uses of the TEC solid supports to perform these functions are shown in the Examples below.

After a biologic sample is procured from an individual, the biological sample and/or the genetic material isolated from it can be correlated (e.g., digitally associated) with the individual. Any suitable method for correlating the biological or genetic sample with the individual from which it was procured can be used, for example by labeling the biological or genetic sample with a unique identifier associated with that individual. The unique identified can be, for example, the individual's name, a numeric or alpha-numeric code, a bar code, or the like. Correlating the individual with the individual's biological or genetic sample can be useful, for example, to allow information pertaining to that individual's genetic and phenotypic make up to be obtained from, and/or provided to, that individual. As such, the database described below includes a field for the unique identifier for the individual as well as fields to store the information in the genetic sample from that individual.

In some embodiments, an individual from whom a biologic sample is procured is prompted to provide certain personal information (as defined herein below) relating to that individual's physical characteristics, including external features such as eye and hair color, height, skin color, gender and the like; internal or occult features or conditions such as non-standard physiologic conditions (e.g., heart murmur or other cardiac condition, placement or absence of organs, and the like); disease state (e.g., cystic fibrosis, multiple sclerosis, cancer, Tay Sachs disease, schizophrenia, depression, and the like); and familial or ancestral history (e.g., occurrence of genetic or physical/mental diseases or disorders in the family, race, country of origin for self and relatives, and the like). In some embodiments, such personal information need not come directly from the individual being tested, but rather it can also be provided on behalf of the individual, for example by medical or birth records, etc., or from others who know the individual and/or have knowledge of their circumstances and background, or some combination. As such, the database described below includes a field for the personal information for the individual.

In various embodiments, the personal information obtained from or on behalf of an individual whose genetic sample is being analyzed is obtained at any time, for example: upon procurement of the biological sample; after procurement of the biological sample but before providing the individual with an analysis of their genetic sample; upon providing the individual with an analysis of their genetic sample, or after providing the individual with an analysis of their genetic sample. In various embodiments, the personal information obtained from or on behalf of the individual is unprompted or generally requested (e.g., "please tell us about yourself and your family"), or can be elicited or otherwise prompted with one or more requests or questions designed to obtain the information. In some embodiments, such requests or questions are presented to the individual (or others with information about the individual) orally or in writing, and the responses is recorded by any suitable technique and entered into the processing system 170. In one embodiment, personal information (as defined herein below) is elicited from an individual through a mobile device application (App) which sends the information for storage in the database 190, in which the individual is allowed to voluntarily participate in one or more surveys which can focus on various aspects of the individual, including physical and mental characteristics, habits, likes and dislikes, familial and ancestral history, and the like. In such embodiments, the personal information provided by the individual through the mobile device application is communicated to a central location, and stored in database 190 with that individual's genetic sample and any information obtained from that sample. As described in more detail below, in some embodiments, the associated genetic information and information provided by the individual, and any analysis of it, is provided to the individual (e.g., be being recalled and displayed through the same mobile device application), for example after being stored in the database 190.

In some embodiments, biologic samples are procured from more than one individual. In certain embodiments, biologic samples are procured from a plurality of individuals, for example several hundred, several thousand, or a million or more individuals. In some embodiments of the method, genetic material from each of the one or more genetic samples procured from the one or more individuals is sequenced using non-targeted, ultra-low coverage sequencing. In one embodiment, the genetic material being sequenced comprises genomic DNA. In another embodiment, the genetic material comprises RNA, for example processed and unprocessed mRNA which is representative of some or all of an individual's genome. The information from these many individuals stored in the database 190 is then used to provide a reference genome or reference panel for a haplotype.

As used herein, "non-targeted" sequencing means sequencing which is not specifically directed, in whole or in part, to any given site or area of the genetic material. "Ultra-low coverage sequencing" refers to the amount of coverage obtained by sequencing with respect to a set of reference genetic material, such as the genome of an organism. Thus, as used herein, "ultra-low coverage sequencing" means that only a fraction of the reference genetic material is represented by the sequenced material from the genetic sample; e.g., about 1× coverage or less of the reference genetic material. In some embodiments, ultra-low coverage sequencing means less than 1× coverage of the reference genetic material, for example about 0.9×, 0.8×, 0.7×, 0.6×, 0.5×, 0.4×, 0.3×, 0.2×, 0.1×, 0.05×, 0.04×, 0.03×, 0.02×, 0.01×, 0.009×, 0.008×, 0.007×, 0.006×, 0.005×, 0.004×, 0.003×, 0.002× or 0.001× coverage of the reference genetic material. As used herein, ultra-low coverage sequencing can also refer to range of coverage of the reference genetic material, for example between about 0.001× to about 1×, about 0.008× to about 0.08×, about 0.01× to about 0.5× and about 0.04× to about 0.4×.

One of ordinary skill in the art can readily determine the sequencing coverage of reference genetic material obtained when sequencing a genetic sample according to the present methods. For example, the number of sequencing reads covering the known polymorphic sites in the one or more reference genomes across the genetic samples being tested can be counted, and the coverage determined by comparing the variation in the number of sequencing reads. An example technique to determine sequencing coverage is shown in Example 4 below.

The present methods thus comprise obtaining a plurality of genetic reads for each of the one or more genetic samples being tested. As discussed above, the ultra-low coverage is determined with reference to a target genome. In one embodiment of the present methods, the genetic material is obtained from contemporary or substantially contemporary sources, and thus is considered to be substantially non-ancient genetic material. One of ordinary skill in the art would understand the difference between substantially ancient and substantially non-ancient genetic material, and can readily identify both. For example, genetic material obtained from living or recently deceased (e.g., about 100 years or less, for example about 25 years less or about 10 years or less) sources is considered to be substantially non-ancient, whereas genetic material obtained from sources over about 100 years old (for example found in archeological sites) is considered to be substantially ancient DNA. Substantially non-ancient DNA also has certain distinguishing characteristics; for example, such genetic material can be substantially intact or non-degraded, or wherein at least about 5% of the genetic material in the sample is derived from the apparent source organism (such as a human), rather than being derived from contaminating organisms such as bacteria and fungi. It is understood that a substantially non-ancient DNA may have small, for example trace, amounts of ancient DNA.

Any suitable technique for sequencing genetic material from the one or more genetic samples can be used in various embodiments of the present methods. Apparatuses and materials for carrying out such sequencing techniques are well-known in the art, and are commercially available. For example, suitable sequencing machines 160 and protocols are available from Illumina, Inc. of San Diego, Calif. as the Illumina MiSeq or Illumina HiSeq 2500. The sequencing results can be in any standard output format that is suitable for storage and retrieval in a database, and/or for further analysis, as are well-known to one of ordinary skill in the art; for example, in FASTQ format. In some embodiments, the output is de-multiplexed, for example so that a single FASTQ file corresponds to a single identified (e.g., barcoded) sample. In one embodiment, genetic material derived from multiple genetic samples is sequenced in a high throughput manner, in order to take advantage of economies of scale. In certain embodiments, sequencing reactions are conducted at a low-volume, e.g., at a volume less than that used for standard sequencing reactions. For example, a low-volume sequencing reaction can be about ½, ⅓, ¼, ⅕, ⅙, ⅐, ⅛, ⅑, ⅒, 1/12, 1/15, 1/20, 1/25 or 1/30 the standard volume for a given reaction. For example, in the context of sequencing reactions used in the present methods, a low-volume reaction can be about 50 microliters ($\mu$l, 1 ml=$10^{-6}$ liters) or less (such as 45 $\mu$l, 40 $\mu$l, 35 $\mu$l, 30 $\mu$l, 25 $\mu$l, 22.5 $\mu$l, 20 $\mu$l, 15 $\mu$l, 10 $\mu$l, 5 $\mu$l, 2.5 $\mu$l, 1 $\mu$l, 0.5 $\mu$l or less than 0.5 $\mu$l. In these embodiments, the low-volume reaction can allow for more reactions to be performed more quickly, and thus achieve low coverage sequencing at a reduced cost.

In some embodiments, sequencing libraries comprising sequenceable material are made from the genetic material from each sample prior to sequencing, using any suitable technique known to one of ordinary skill in the art, including the fragmentation, tagging of genetic material with sequencing adaptors to provide sequenceable material, and may optionally include any subsequent amplification of the genetic material (e.g., DNA) comprising the genetic sample. Suitable library preparation techniques are described in, for example, Picelli S et al. (2016), Tn5 transposase and tagmentation procedures for massively scaled sequencing projects, Genome Research 24:2033-2040; Baym M et al. (2015), Inexpensive multiplexed library preparation for megabase-sized genomes, PLosOne 10(5): e0128036 (DOI: 10.1371/journal.pone.0128036; and Adey A et al. (2010), Rapid, low-input, low-bias construction of shotgun fragment libraries by high-density in vitro transposition, Genome Biology 11:R119, the entire disclosures of which are herein incorporated by reference. Suitable materials and protocols for library preparation are also commercially available, such as the Nextera XT DNA library prep Kit from Illumina, Inc. (San Diego, Calif.), which can be used according to the manufacturer's protocol, and which combines the steps of DNA fragmentation, end-polishing, and adaptor-ligation into one step called "tagmentation" (see, e.g., Picelli S et al. (2016), supra).

In certain embodiments of the present methods, the library preparation, amplification and/or sequencing steps are carried out in low-volume reactions. As used herein, a "low-volume" reaction means that the total reaction volume is less than that of the standard reaction. In some embodiments, a low-volume reaction can be about ½, ⅓, ¼, ⅕, ⅙, ⅐, ⅛, ⅑, ⅒, 1/12, 1/15, 1/20, 1/25 or 1/30 of the standard reaction volume. For example, in the context of library preparation and/or amplification reactions used in the present methods, a low-volume reaction can be about 50 $\mu$l or less, such as 45 $\mu$l, 40 $\mu$l, 35 $\mu$l, 30 $\mu$l, 25 $\mu$l, 22.5 $\mu$l, 20 $\mu$l, 15 $\mu$l, 10 $\mu$l, 5 $\mu$l, 2.5 $\mu$l, 1 $\mu$l, 5 $\mu$l or less than 0.5 $\mu$l. In one embodiment, about ⅛ of all volumes specified in the Illumina Nextera XT DNA library prep Kit manufacturer's protocol can be used in sequencing reactions of the present methods. In these embodiments, the low-volume reaction can allow for more reactions to be performed more quickly, and at a reduced cost. Sequencing libraries made according to the present methods can be further analyzed prior to sequencing, for example by determining the nucleic acid size concentration or size distributions, and can optionally be pooled prior to sequencing.

In some embodiments, sequencing reads obtained are aligned to a reference genetic material, for example to one or more reference genomes. The one or more reference genomes can be the genome corresponding to the organism of the individual from which the genetic sample was obtained (e.g., a human reference genome if the individual is human), or these can be reference genomes corresponding to organisms which are different from the individual from which the genetic sample was obtained. Example human reference genomes suitable for use in the present methods, including the hg19 human reference genome that can be accessed online, for example, from the University of Santa Cruz Genome Browser (see, e.g., UCSC Genome Browser: Kent W J et al., The human genome browser at UCSC. Genome Res. 2002 June; 12(6):996-1006). In some embodiments, the one or more reference genomes can be the genomes of bacteria, protists, fungi, plants, parasites and/or other organisms, or combinations of two or more genomes from organisms falling within these categories. Such reference genomes are also readily available through public resources, such as the University of Santa Cruz Genome Browser.

Suitable publicly- or commercially-available algorithms for aligning sequencing reads to reference genomes according to the present methods used in various embodiments, are well-known to those of ordinary skill in the art, and include, for example, the "bwa-mem" algorithm (arXiv: 1303.3997) available online through the Cornell University Library. Obtaining aligned sequencing reads against one or more non-human reference genomes at one time can be accomplished using, for example, the Kraken software tools and alignment protocols as described in Wood D E and Salzburg S L (2014), Kraken: ultrafast metagenomic sequence classification using exact alignments, Genome Biology 15:R46.

Thus according to some embodiments, a plurality of genetic reads is obtained by sequencing each of the one or more genetic samples and aligning the sequencing reads with one or more reference genomes, which can be the same or different as the genome of the individual from which the genetic sample was obtained. As used herein, the genome of the individual from which the genetic sample was obtained is sometimes referred to as the "target genome." The plurality of aligned genetic reads produced by aligning the sequencing reads with one or more reference genomes can be used to obtain genetic information about the individual from which the genetic sample was obtained, and/or about organisms associated with that individual. Organisms associated with the individual from which the genetic sample was obtained can include the microbiome of that individual's mouth, or organisms which that individual had recently consumed, traces of which still remain in the individual's oral cavity. Thus, in some embodiments, the one or more reference genomes for use in the present methods are of food origin. The genetic information thus obtained can be used to construct a genotype of the individual, and/or of the organisms associated with the individual. An example method to determine genotypes of organisms associated with an individual from which a genetic sample was obtained is shown in Example 6 below. In some embodiments of the present methods, the one or more genetic samples are assigned to one or more genotypic or phenotypic groups or the presence of one or more allelic variants is determined, based on the aligned genetic reads. In various embodiments, such genotypic or phenotypic groups include any group which can be associated with certain genetic traits, and/or certain phenotypic traits associated with those genetic traits, as determined by the present methods; for example, familial groups or relatedness, ancestral groups, disease groups or disease risk groups.

In another example embodiment, genetic information is obtained with genetic reads aligned to a human reference genome and compared against a reference set of known polymorphic genetic sites, for example as available online from The International Genome Sample Resource as the 1000 Genomes Project, Phase 3. In this embodiment, for each sample at each known variable position, a single read covering the position (if there was at least one) can be sampled and the base of the read noted. These reads are aligned with the reference set, and genetic information obtained from the reads covering the polymorphic genetic sites. Such information is used to determine, for example, an individual's ancestry (as shown below, for example, in Example 4).

It is not necessary in the present methods to use genotype imputation to infer genotypes of the individual from which the genetic sample was obtained, or of organisms associated with that individual, as the methods are robust enough to produce sufficient information to obtain such genotypes even though only ultra-low coverage sequencing is employed. Thus, the present methods are able to identify one or more rare allelic variants in individual from which the genetic sample was obtained, or from organisms associated with that individual, even if the allelic variant was previously unknown. Such rare allelic variants can be, for example, rare variants associated with a disease or disorder, sometimes termed herein a "rare disease variant." The presence of a disease variant in the genotype of an individual, as identified or confirmed according to the present methods, allows that individual to be assigned to a disease group (if the disease is apparent or has manifested) or a disease risk group, if that disease has not yet become apparent or has not yet manifested. Disease carrier status of individuals can also be ascertained according to the present methods.

In some embodiments of the present methods, genotype imputation can be used if desired. An example method employing genotype imputation is shown in Example 3 below. In this example method, a reference set of known polymorphic genetic sites can be obtained (for example, from the 1000 Genomes Project, Phase 3). A genotype likelihood can then be calculated for each sample, for each of the known variable sites covered by at least one sequencing read. This genotype likelihood corresponds to the probability of each true genotype for each individual, given the observed sequencing reads. Imputation from the genotype likelihoods can be performed using any suitable technique, for example with publicly-available algorithms such as the BEAGLE software (as described in Browning B L and Yu Z (2009), Simultaneous genotype calling and haplotype phasing improves genotype accuracy and reduces false-positive associations for genome-wide association studies, Am J Hum Genet. 85(6):847-61), and the reference set of polymorphic genetic sites. These methods are based on determining an imputed genotype of the individual by calculating a probability of the one or more reference genomes based on the plurality of aligned reads, and setting the reference genome with a highest probability as the imputed genotype. Using this example method, a set of genetic variants with high predicted imputation quality ($r^2 > 0.8$ for the predicted correlation between the true allelic dosage and the imputed allelic dosage) can be obtained.

In some embodiments, the present methods are used with genotype imputation to identify cryptic ancestral relatedness between at least two genetic samples, one genetic sample procured from a first individual having a first genotype and a second genetic sample procured from a second individual having a second genotype. The degree of relatedness between the first and second individuals is determined by comparing mapped genetic reads from both individuals that cover known polymorphic genetic sites in a reference human genome. In an example method, the polymorphic genetic sites covered by at least one sequencing read in each individual being tested is identified, a single sequencing read from each can be sampled, and the value (base) at the site noted. In certain embodiments, the site is additionally labeled according to its allele frequency in a reference dataset, for example the entire 1000 Genome Project Phase 3 dataset. A predetermined set of polymorphic sites with a predetermined minor allele frequency, for example between 1% and 10%, is extracted, and the set of sites where the sampled allele from both individuals which match the known minor allele is determined. The concordance between these allele(s) in the two individuals provides an indication of the degree of relatedness between the two individuals. For example, if the two individuals are a parent-child pair (related to one generation), a random rare allele sampled from each of these individuals should match about 50% of the time. Likewise, for a grandparent-grandchild pair (related to two generations), a random rare allele sampled from each of these individuals should match about 25% of the time. For individuals related to three generations, a random rare allele samples from each of the individuals should match about 12.5% of the time. For individuals related to four generations, a random rare allele samples from each of the individuals should match about 6.25% of the time. For individuals related to five generations, a random rare allele samples from each of the individuals should match about 3.125% of the time. All these are large compared to the rate of occurrence of an allele that is known to occur in only 1% of the population, and indicate a probability of relatedness. Thus in some embodiments, the degree of relatedness to a predetermined number of generations can be determined, for example no relatedness, or relatedness to within 1, 2, 3, 4, 5 or more generations.

Structural Components

In the illustrated embodiments, the genetic and personal information obtained from or on behalf of a plurality of individuals, or from organisms associated with the plurality of individuals, obtained in various embodiments, is compiled into the database 190 comprising such information. In the database 190, each genetic sample is identified as corresponding to a different individual. Likewise, any genetic information (including any genotype information) for a given individual obtained from that genetic sample, and any information provided by or on behalf of that individual, is associated in the database with that genetic sample and/or that individual.

As used herein, "personal information" of an individual is any information provided directly by an individual, or on behalf of an individual (for example by others familiar with that individual or their circumstances, or from medical or other records pertaining to that individual). In various embodiments, such personal information includes information regarding an individual's external physical characteristics, such as eye and hair color, height, skin color, gender and the like; internal or occult physical features or conditions such as non-standard physiologic conditions (e.g., heart murmur or other cardiac condition, placement or absence of organs, and the like); disease state (e.g., cystic fibrosis, multiple sclerosis, cancer, Tay Sachs disease, schizophrenia, depression, and the like); habits; likes and dislikes; and information about other individuals or groups associated with the individual, such as familial or ancestral history (e.g., occurrence of genetic or physical/mental diseases or disorders in the family, race, country of origin for self and relatives, and the like). Personal information of an individual is sometimes referred to herein as "phenotypic information" of that individual.

In some embodiments, personal and genetic information are procured from more than one individual according to the present methods, for example from several hundred, several thousand, or a million or more individuals, and stored in the database 190. A database according to such embodiments is used to store and retrieve personal and genetic information for an individual, compare that individual to others in the database, and provide such information to the individual or others upon request. The database 190 is used in some embodiments to help analyze one or more genetic samples according to the present methods, by use of the database 190 as a reference set of phenotypic or genetic traits associated with a given genotype, individual or group. The greater the amount of personal and genetic information correlated and stored within the database 190, the more accurate and useful the database 190 is as a reference set. Thus some embodiments also provide a method of creating a database comprising genetic and personal information obtained from or on behalf of a plurality of individuals, or from organisms associated with the plurality of individuals, which information is obtained through the present methods. The information for each of the one or more genetic samples is associated with personal information, if any, provided by or on behalf of the individual corresponding to the genetic sample, and the personal and genetic information comprising the database is stored in a manner in which it can be retrieved and manipulated. As used herein, information is "manipulated" by subjecting the information to any analysis, comparison, transformation, transmission, display or any combination thereof, or any other handling, management or use of the information.

A database in some embodiments is implemented using the specific techniques described here and maintained in any suitable manner as is well-known in to one of ordinary skill in the art, including as an apparatus; a system; a computer program product embodied on a computer readable storage medium; and/or one or more processors, wherein the one or more processors are specifically configured to execute instructions specific to this embodiment, wherein such instructions are stored on and/or provided by memory coupled to the processor. A component of a database, such as the one or more processors or memory described as being configured to perform a task can be implemented as a general component that is temporarily configured to perform the task at a given time, or can be a specific component that is manufactured to perform the task. As used herein, the term "processor" can mean one or more devices, circuits, and/or processing cores configured to manipulate information, such as computer program instructions. One of ordinary skill in the art would recognize that a database can comprise various components in any suitable configuration and relationship which allows the specific functions described herein to be carried out using the database.

Figure 2:
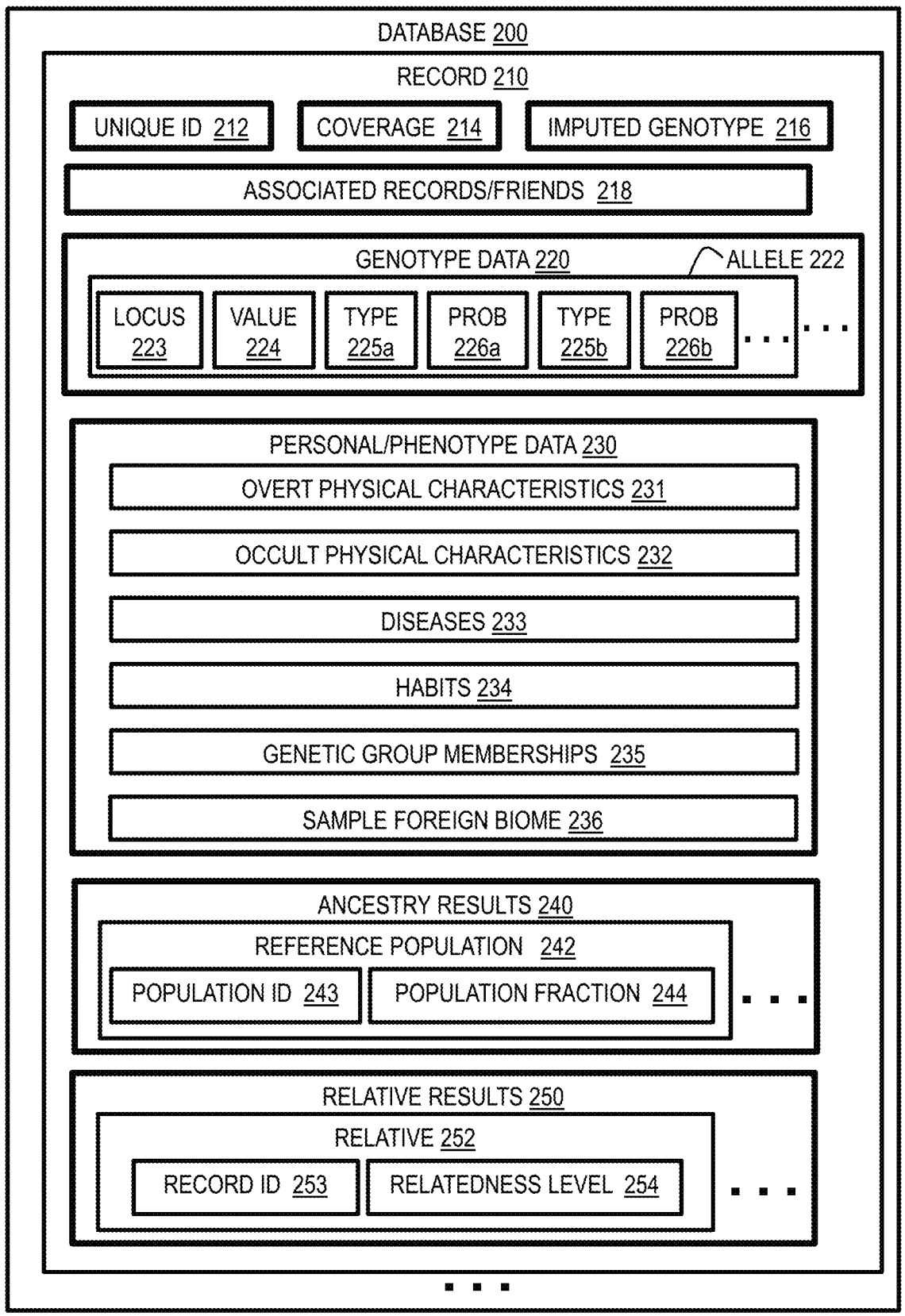
FIG. 2 is a block diagram that illustrates an example database for storing the data determined by the processes described herein, according to an embodiment.

FIG. 2 is a block diagram that illustrates an example database 200 for storing the data determined by the processes described herein, according to an embodiment. Thus, database 200 is a specific embodiment of database 190 depicted in FIG. 1D. Although fields are depicted in FIG. 2 as integral blocks in a particular order, for purposes of illustration, in other embodiments, one or more fields or portions thereof are stored in a different order on one or more devices with pointers to maintain the associations depicted, or one or more other fields are added, or two or more fields or portions thereof are merged, or one or more field or portions thereof are omitted.

Database 200 includes one or more records, including record 210 among others indicated by ellipsis outside record 210. Each record includes one or more fields, such as unique ID field 212, coverage field 214, imputed genotype field 216, associated record/friends field 218, genotype data field 220, personal/phenotype data field 230, ancestry results field 240 and relative results field 250.

Unique ID field 212 holds data that indicates a particular subject or individual from whom a genetic sample was taken. As described above the data in the field can indicate a name, date of birth, social security number, phone number, a unique or serial number assigned by the low coverage condition inference module 172, other indicator, or some combination. The actual low coverage sequence data collected is stored in the genotype data field 220, which indicates the values of the alleles detected among the low coverage aligned reads, described in more detail below. The coverage field 214 holds data that indicates how much of a reference genome is sampled by the genotype data in field 220. The imputed genotype holds data that indicates a reference genotype imputed to the individual identified in field 212 based on the low coverage genotype data in field 220. In some embodiments in which an imputed genotype is not determined, the imputed field 216 is omitted or contains a null value. The associated record/friends field 218 includes data that indicates one or more other individual in the database associated with the current individual by choice, e.g., friends or family members or doctors or caregivers who want to have their ancestries compared or relatedness determined or be informed of information in one of the other fields.

The genotype data field 220 holds data that indicates information about each allele detected among the low coverage aligned reads. Each allele has it own set of fields collected into an allele field 222 among other indicated by ellipsis outside field 222 and inside field 220, collectively referenced hereinafter as allele fields 222. In the illustrated embodiment, each allele field 222 includes a locus field 223, a value field 224, and one or more pairs of genotype and genotype probability fields, such as genotype field 225a, probability field 226, genotype field 225b, probability field 226b, among others indicated by ellipsis inside allele field 222, and collectively referenced hereinafter as type fields 225 and probability fields 226, respectively. The locus field 223 indicates the position of the allele on the reference genome, e.g., the chromosome number and start location expressed as a base number or as a serial number for the order of the allele on the chromosome, such as 1 for the first allele, 2 for the second allele, etc. The value field 224 holds data that indicates the base found at the position, such as A, C, G, or T, or such as 0 for the dominant allele and 1 for the minor allele for a given population or reference genome. If multiple reads cover the same then in different embodiments, the variants from the multiple different reads are used differently. In some embodiments, a read is selected at random from all the reads that cover the allele, and the variant for the randomly selected read is stored in field 224 of the database. In other embodiments, a consensus value of all read values for that allele is stored in the field 224, which is the most common variant among the reads is stored. In some embodiments, all values detected for that allele are stored in the database in several fields 224 for each allele field 222; and, in some of these embodiments associated with each field 224 for the same allele is a count in a variant count field (not shown). Different values for the same allele in different reads of the low coverage sequencing indicate that the subject is heterozygous for that allele. In some embodiments, the genotype data field further holds data that indicates, for each allele in each imputed genome for each aligned read, the allele and a genotype and a probability of that genotype for all possible genotypes.

Given a particular value, or values, at a particular location the allele can indicate one or more of several known genotypes. A known possible genotype is indicated in the type fields 225; and the probability that the allele value is associated with that type is indicated in the corresponding probability field 226 paired with the type field 225. The pair is repeated at least for each genotype associated with the value at that allele. These probabilities are used to infer a condition of the individual associated with record 210, such as the most probable one or more genotypes, given all the measured allele values, as described in more detail below.

The personal/phenotype data field 230 holds non-sequence data about the individual that is associated with the record 210, such as the kind of phenotype and personal data listed above. In the example embodiment, the personal/phenotype data field includes an overt physical characteristics field 231, an occult physical characteristic field 232, a diseases field 233, a habits field 234, a genetic group memberships field 235, and a sample foreign biome field 236. The overt physical characteristics field 231 holds data that indicates a parameter type and a value for that parameter, such as data that indicates the parameter is hair color and the value is black Any method known in the art can be used to format the data in the field, such as subfields or XML formatted text. In some embodiments, the parameters are indicated by the order of the values. The remaining fields may be formatted in any way known in the art, including subfields or XML formatted text for parameter only or parameter-value pairs. The occult physical characteristics field 232 holds data that indicates a parameter such as missing appendix, or right-side placement of heart. The diseases field 233 holds data that indicates chronic diseases suffered by the individual as described above, such as cystic fibrosis, diabetes and leukemia. The habits field 234 holds data that indicates any behavioral patterns for the individual, such as early riser, regular exerciser, preferences for certain foods, any addictions to drugs, moodiness, optimism, snoring, allergies, medications, place of residence, places traveled to, religious practice, level of education, subjects of any specialized degrees, among others. The genetic group membership field 235 holds data that indicates any genetic groups to which the individual belongs, with characteristics the individual might or might not possesses, such as family history of disease, race, familial country of origin, among others. The sample foreign biome field 236 holds data that indicates organisms different from the individual to which genetic material was found in the genetic sample taken from that individual, such as biome of organisms and foodstuffs found in saliva, probiotics in samples from the gut, and malaria or trichinosis or other parasite organisms found in blood or tissue samples.

The ancestry results data field 240 holds data that indicates the results of any ancestry analysis performed by the low coverage condition inference module 172 for the individual that is associated with the record 210. In the illustrated embodiment, the ancestry results data field 240 holds data that indicates information about each reference population type used in the embodiment, such as reference ethnic populations or reference disease risk populations or some combination. Each reference population has it own set of fields collected into reference population field 242 among others indicated by ellipsis outside field 242 and inside field 240, collectively referenced hereinafter as reference population fields 242. In the illustrated embodiment, each reference population field 242 includes a population identification (ID) field 243, and a population fraction field 244. The population ID field 243 holds data that indicates one of the reference populations, such as an African population of the multiple ethnic reference populations, or a breast cancer risk population of the multiple disease risk reference populations. The population fraction field 244 holds data that indicates the fraction of the genome of the individual that matches that reference population based on the low coverage sequencing data for the individual. A method to determine this result stored in field 244 is described below with reference to FIG. 4.

The relative results data field 250 holds data that indicates the results of any relatedness analysis performed by the low coverage condition inference module 172 for the individual that is associated with the record 210. In the illustrated embodiment, the relative results data field 250 holds data that indicates information about the relatedness of zero or more other individuals in the database, such as one or more individuals selected from the associated records/friends field 218. Each selected individual has it own set of fields collected into relative field 252 among others indicated by ellipsis outside field 252 and inside field 250, collectively referenced hereinafter as reference relative fields 252. In the illustrated embodiment, each relative field 252 includes a database record identification (ID) field 253, and a relatedness level field 254. The record ID field 253 holds data that indicates another individual in the database by the contents of the unique ID field 212 for that other individual. The relatedness level field 254 holds data that indicates the degree of the relatedness of the individual to the other individual indicated by field 253. A method to determine this result stored in field 254 is described below with reference to FIG. 5 for relatedness out to about 3 generations and FIG. 6 for relatedness out to at least 5 generations.

Figure 8A:
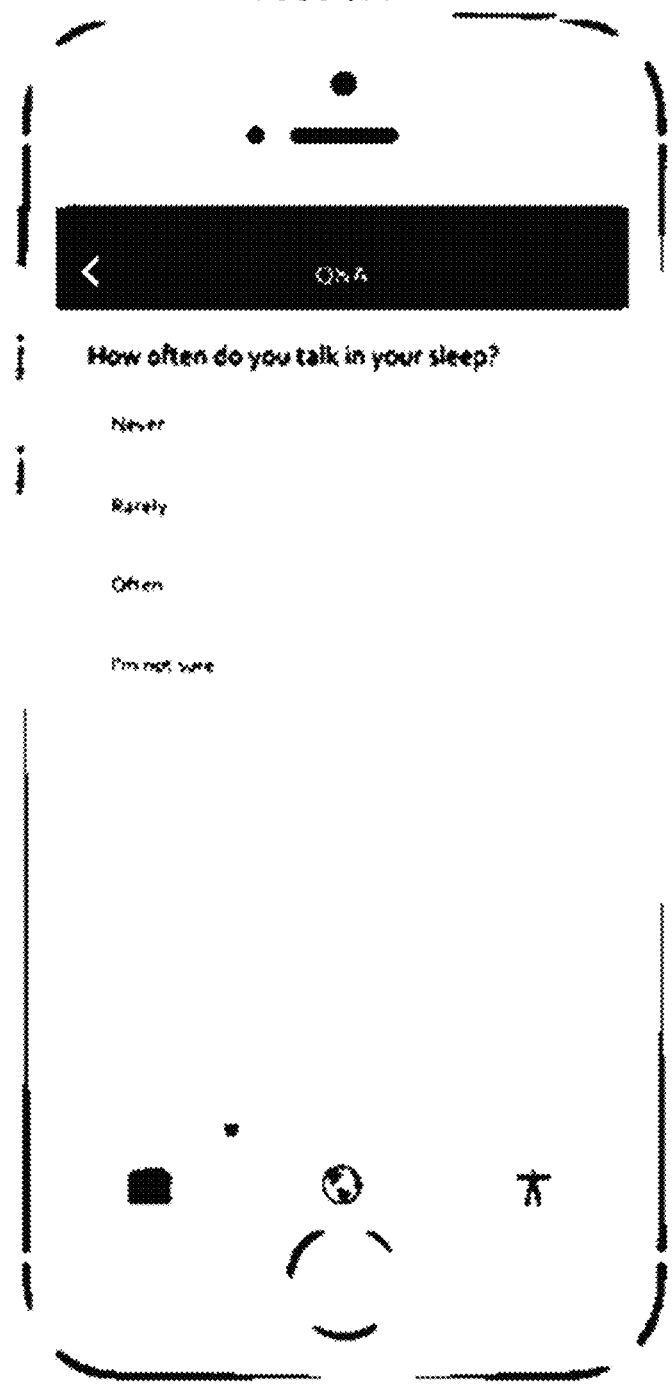
FIG. 8A is an example user interface for displaying on a personal mobile device via a mobile device application, for collecting personal information according to the present methods.

In one embodiment, at least some of the personal and genetic information comprising the database 190 is transmitted to and from a personal mobile device, such as a smart phone, tablet or personal fitness device, e.g., a FitBit (FitBit, Inc., San Francisco, Calif.) or an Apple Watch (Apple, Inc., Cupertino, Calif.). As discussed above, a mobile device application can be provided for downloading onto a personal mobile device. This mobile device application can provide a number of user interfaces, which can prompt individuals to enter in personal information which can be transmitted to and stored in a database of the embodiment, to be correlated with their genetic information. An example user interface for gathering personal information according to the present methods, displayed by on a personal mobile device by a mobile device application, is shown in FIG. 8A.

The mobile device application can also be used to solicit, initiate and/or receive requests from an individual for analysis of their genetic material. For example, an individual can initiate and pay for an analysis of their genetic material through various user interfaces on the mobile device application. Functions within the mobile device application can then instigate shipping of a biological sample collection device (such as a saliva collection tube) to the individual, with instructions on how to collect the biological sample, and where to ship the sample for further processing. Functions within the mobile device application can also notify the individual when their genetic information, obtained by the present methods, is ready to be viewed.

The mobile device application can also be used to provide information to an individual, for example, by allowing the individual to access and view their results from the genetic analysis and/or correlation of that genetic information with their personal information in the database. For example, the individual can access information relating to their ancestry, which was obtained by analysis of their genetic material according to the present methods. FIG. 2A shows an example user interface where such ancestry information is displayed. An individual can also access, for example, information relating to other organisms associated with their genetic sample, such as the composition of their mouth microbiome (provided in this case, e.g., that the individual has provided an appropriate biological sample, such as a saliva sample). FIG. 2B shows an example user interface displaying mouth microbiome information for an individual.

Information in a database, according to some embodiments can also be manipulated to compare results from one individual to results from one or more other individuals in the database. Such comparisons can be provided to the respective individuals through a user interface, such as one provided via a mobile device application. For example, an individual can add others who have had their genetic material analyzed by the present methods (and have had that information added to the database) identified as "friends" within the mobile device application and/or the database and stored in field 218. The individuals so designated as "friends" can see their own information (e.g., ancestry or mouth microbiome) and those of their "friends." An individual using the mobile device application can also, for example, create a composite ancestry that might represent the ancestry of a hypothetical child between themselves and another individual in the database. It is understood that any functions of the mobile device application described herein, as well as any functions, interactions or information manipulations performed by a database of the embodiment, can also be accomplished through any suitably configured electronic device, such as a personal computer properly and unconventionally configured to perform the functions described herein.

Methods

Figure 3:
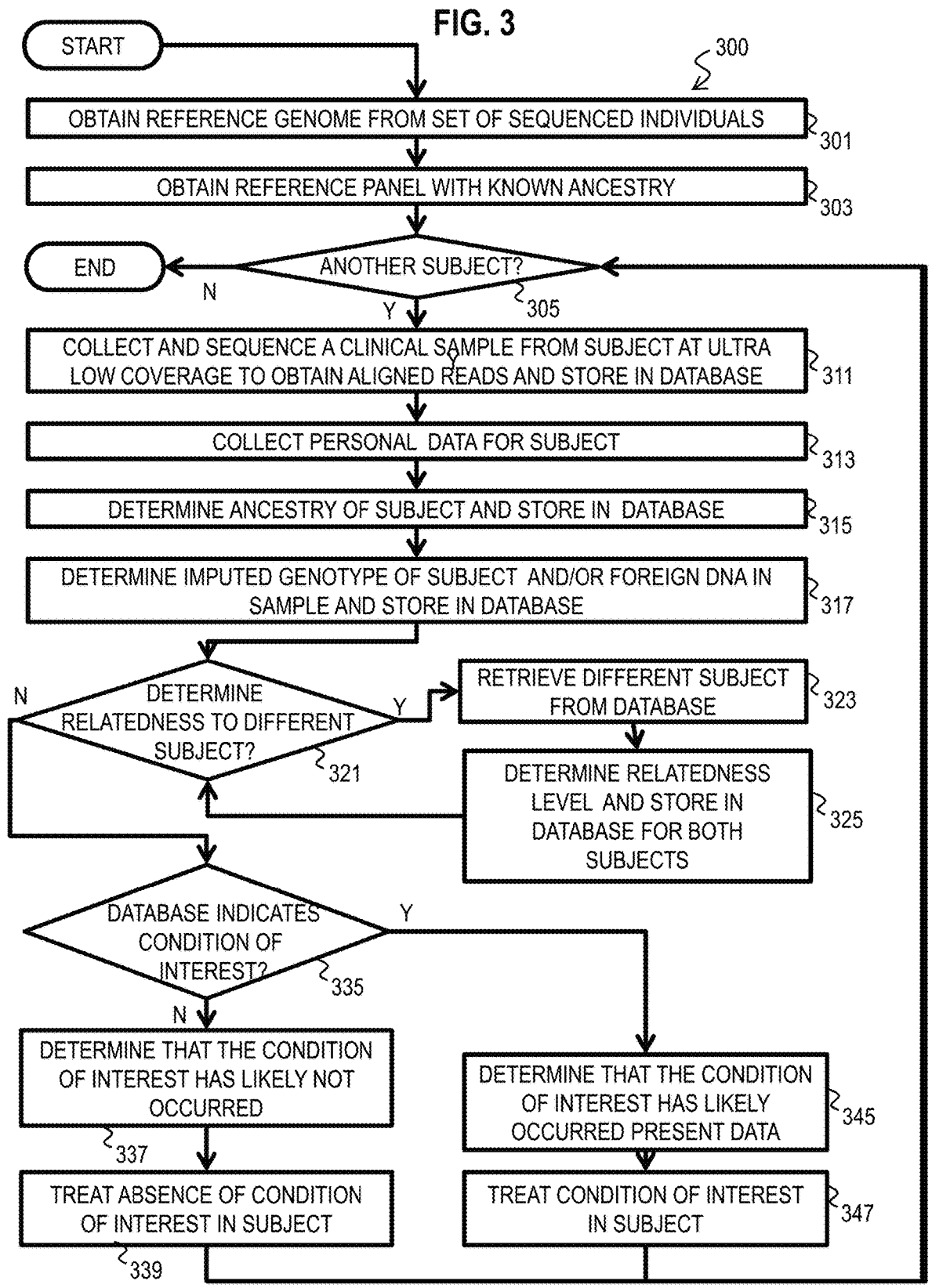
FIG. 3 is a flow diagram that illustrates an example method for collecting aligned reads from ultra low coverage sequencing data, determining conditions, and storing and using the data determined, according to an embodiment.

FIG. 3 is a flow diagram that illustrates an example method 300 for collecting aligned reads from ultra low coverage sequencing data, determining conditions, and storing and using the data determined, according to an embodiment. Although steps are depicted in FIG. 3, and in subsequent flowcharts FIG. 4 through FIG. 7, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301 a reference genome is obtained from a set of sequenced individuals. In some embodiments, the reference genome is obtained from a published or publicly available or privately available source based on whole genome sequencing (WGS), which is conventionally high coverage genome sequencing. In other embodiments, the reference genome is generated from hundreds, thousands or millions of individuals subjected to low coverage sequencing and already stored in the database 190. In some embodiments, step 301 includes obtaining reference genomes for a variety of organisms that might be in the sample obtained from the subject, some as reference sequences for certain diseases (e.g., tumor cells), parasites (e.g., malaria) or other different species (e.g., common bacteria, viruses, fungi, and foodstuffs). In step 303, a reference panel sequence for a haplotype associated with one or more particular ancestries is obtained. In some embodiments, the reference panel is obtained from a published or publicly available or privately available source based on whole genome sequencing (WGS), which is conventionally high coverage genome sequencing. In other embodiments, the reference panel is generated from hundreds, thousands or millions of individuals subjected to low coverage sequencing and already stored in the database 190.

In step 305, it is determined whether there is another subject to be sampled. Any method may be used to determine if there is another subject. For example, a sample can arrive from a prospective customer or client via a self sample mailed or a sample provided by a healthcare worker, with any required payment. In some embodiments, a message can be received from a remote computer or processor operated by a person who wishes to submit a sample for himself or herself or for another person. In response, a sample kit is sent to the person and upon receipt of the sample kit with sample included, and any payment required, another subject is available for processing. If there is not another subject, the process ends. If so, the process continues with step 311.

In step 311, the clinical sample from the subject is collected and sequenced at low coverage, such as ultra low coverage and processed using conventional means to obtain a set of aligned reads. The reads are stored unconventionally in a database, such as in genotype data field 220, described above, for a record 210 for the subject. In some embodiments, step 311 includes generating the contents for the unique ID field 212 and storing that in the same record. In some embodiments, step 311 includes determining the actual degree of coverage obtained from processing the sample and storing data that indicates that value in field 214. For example, in some embodiments, the coverage is determined as number of alleles stored in genotype data field 220 divided by the number of alleles in the reference genome.

In step 313, personal data is collected for the subject whose sample was processed in step 311. Various ways were discussed above on how to obtain that information, such as from the subject himself or herself, from a guardian, from a caregiver, from public sources. The information collected here is stored in personal/phenotype data field 230. In some embodiments, at least some information is obtained through a user interface on a mobile device in the hands of the subject or other person. The mobile device is on the local or private network 1380 or internet or cell phone network 1390 depicted in FIG. 13 as part of the processing system 170. A client process operating on the mobile device prompts for and/or otherwise obtains the input from a person at a remote site and communicates that data using messages with a server process operating at some central or distributed site. Both the client process and server process in such embodiments are components of the low coverage condition inference module 172.

Figure 8B:
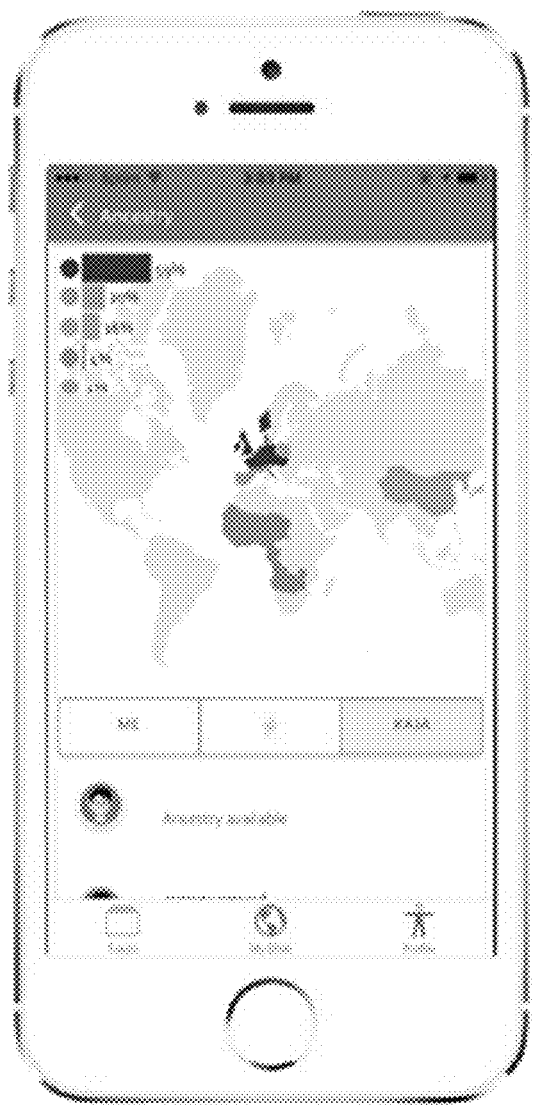
FIG. 8B is an example user interface for displaying ancestry information for an individual on a personal mobile device.
Figure 8C:
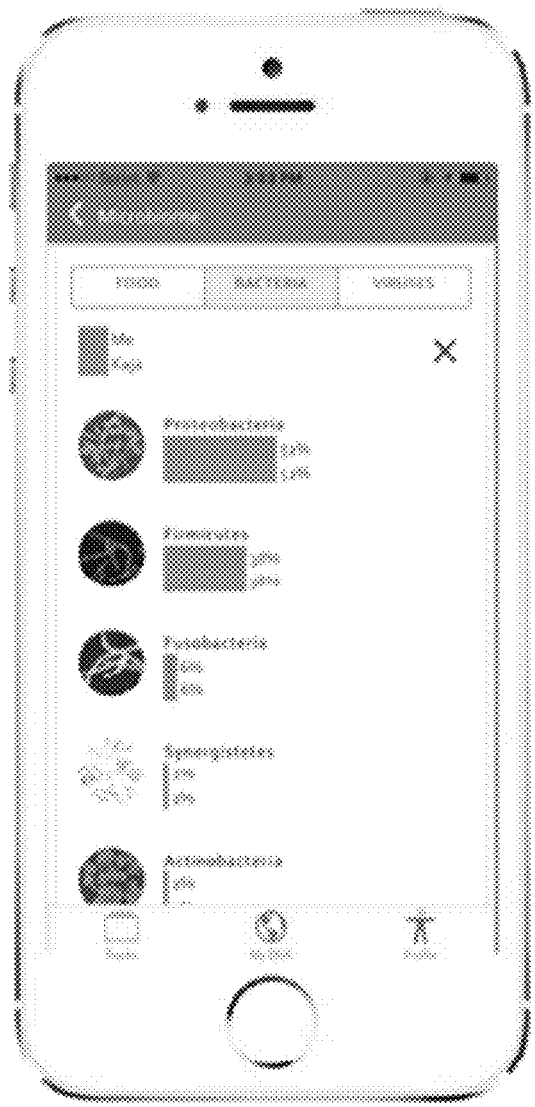
FIG. 8C is an example user interface for displaying mouth microbiome information associated with an individual on a personal mobile device.
Figure 9:
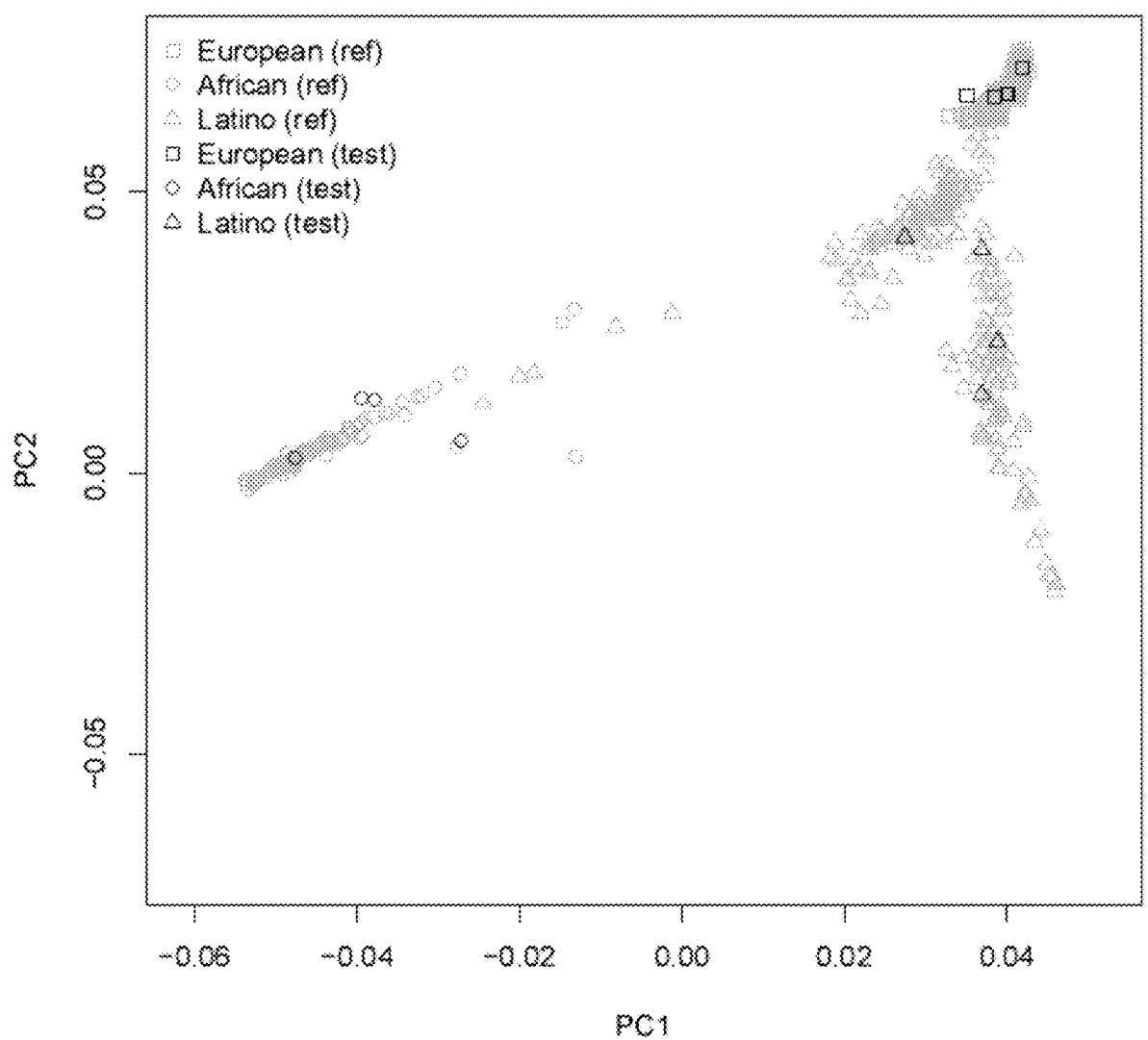
FIG. 9 is a graph representing the principal component analysis of 1000 Genome Project samples using an example embodiment of the method.

FIG. 8A through FIG. 8C and FIG. 11 are diagrams that illustrate example screens on a display device of processing system 170, according to various embodiments. The screen includes one or more active areas that allow a user to input data to operate on data. As is well known, an active area is a portion of a display to which a user can point using a pointing device (such as a cursor and cursor movement device, or a touch screen) to cause an action to be initiated by the device that includes the display. Well known forms of active areas are stand alone buttons, radio buttons, check lists, pull down menus, scrolling lists, and text boxes, among others. Although areas, active areas, windows and tool bars are depicted in FIG. 8A through FIG. 8C as integral blocks in a particular arrangement on particular screens for purposes of illustration, in other embodiments, one or more screens, windows or active areas, or portions thereof, are arranged in a different order, are of different types, or one or more are omitted, or additional areas are included or the user interfaces are changed in some combination of ways.

FIG. 8A is an example user interface for displaying on a personal mobile device via a mobile device application, for collecting personal information, according to the present methods. In FIG. 8A, the user interface includes a header bar indicating that a client process of the low coverage condition inference module 172 is currently operating on the remote or mobile device. A prompt is presented on the display of the remote or mobile device requesting specific or general information for the personal/phenotype data field 230. In the illustrated embodiment, a prompt is presented for how often the subject talks during sleep. A radio button list of choices is provided to receive the response as input from the user. In some embodiments, during step 313, the user identifies one or more other subjects who are, or might be, in the database, and who may be relatives. Then, identifiers for those identified subjects are stored in associated records/friends field 218.

Returning to the method 300 in FIG. 3, in step 315, the ancestry of the subject is determined and stored in the database, e.g., in field 240, which indicates, for each of one or more ancestry population reference panels, the fraction of the subject's alleles attributable to that population. A novel method to determine such fractions with low coverage sequencing data and without genotype imputation is described in more detail below with reference to FIG. 4. The ancestry results are eventually presented on a display device (see for example, steps 337 and 345, described below). FIG. 8B is an example user interface for displaying ancestry information for an individual on a personal mobile device. The user interface includes a header bar indicating a client process of the low coverage condition inference module 172 is currently operating on the remote or mobile device. A map is displayed that highlights the geographical areas where the subject shares alleles with ancestry reference panels for populations that are characteristic of those areas. The fraction of each ancestry reference pane in the subject's low coverage sequencing data is indicated by a bar graph superimposed on the map.

Returning to the method 300 in FIG. 3, in step 317, an imputed genotype for the subject is determined, or the occurrence of foreign DNA is determined, or some combination. In some embodiments, the determination of an imputed genome or foreign DNA is not desired and step 317 is omitted. A novel method to determine an imputed genome using low coverage sequencing data is described below with reference to FIG. 5. FIG. 8C is an example user interface for displaying mouth microbiome information associated with an individual on a personal mobile device, according to some embodiments. The user interface includes a header bar indicating a client process of the low coverage condition inference module 172 is currently operating on the remote or mobile device. The fraction of each non-human organism in the subject's sample's low coverage sequencing data is indicated by a bar graph labeled with a name of the organism. In the illustrated embodiment, each bar is also labeled with a numerical value for the fraction; and, an icon representing the organism is displayed next to the bar graph. In some embodiments, the icon is an active area that the user can select to obtain more information about the organism.

Returning to the method 300 in FIG. 3, in step 321, it is determined whether it is desired to determine the relatedness to another subject for which data is already or may in the future be stored in the database 190. Any method may be used to determine this. In some embodiments, every new subject is compared to every previously stored subject automatically, or to every subject identified in the associated records/friends field 218, or every subject that includes the current subject in their field 218; and, step 321 is omitted and control passes directly to step 323. In some embodiments, the user is prompted through a user interface on a remote or mobile device to input the name or identifier of another person who might be in the database already. In some embodiments, data identifying subjects already identified in the associated records/friends field 218 are presented to the user on a local or remote or mobile device for the user to select. For example, a radio button list labeled with data that identifies subjects in the field 218 is presented to the user; and, the user selects one or more subjects to which relatedness is to be determined. If it is desired to determine the relatedness to no other subject, or if no other subject remains to which relatedness is to be determined, control passes to step 335, described below. Otherwise, control passes to step 323. Steps 323 and 325 are repeated for each different subject to which relatedness to the current subject is to be determined.

In step 323, data is retrieved for a different subject in the database 190, wherein the different subject is one of the different subjects identified in step 321. For example, all or part of the record 210 for the different subject is retrieved from database 200. In step 325, the relatedness level between the current subject and the different subject is determined. A novel method to determine level of relatedness without imputing a genotype is described below in more detail with reference to FIG. 6. This method has been found effective for at least 3 levels of relatedness. Another novel method to determine level of relatedness using imputed genotype is described below in more detail with reference to FIG. 7. This method has been found effective for at least 5 levels of relatedness. Either or both methods are used in various embodiments of step 325. In various embodiments, data indicating the different subject and the level of relatedness are presented on a display device, such as on a local or remote or mobile device with a display component.

When no other subjects are left to which to determine relatedness, control passes to step 335. In step 335, it is determined whether the condition of interest has occurred. For example, in various embodiments, it is determined that the subject has a particular ancestry, or belongs to a particular imputed genotype, or has a certain level of relatedness to another individual, or has a particular different species in the genetic sample collected in step 311. In some embodiments, this determination is based on further processing of the earlier results, e.g., in a statistical model of the conditions being searched for.

If it is determined in step 335 that the condition of interest is not indicated, then in step 337 it is determined that the conditions of interest likely has not occurred in the subject. In step 339 the subject is treated as if the condition of interest has not occurred. For example, the information is presented on a display and conveyed to the subject. In some embodiments, the data displayed include data indicating the conditions discovered which are not of interest If, however, it is determined in step 335 that the condition of interest is indicated (such as membership in a genotype associated with a disease), then in step 345 it is determined that the conditions of interest likely has indeed occurred in the subject. In step 347, the condition of interest is treated by any method known for the condition of interest. For example, the information is presented on a display and conveyed to the subject, and a treatment plan for the condition of interest is presented, or the treatment is begun, or some combination.

Using the method 300, low coverage sequencing data is effective for determining certain conditions of interest. Both the sensitivity and accuracy are improved over previous methods using low coverage sequencing data. In addition, the results are surprising competitive with more expensive and tedious operations, involving targeted sequencing or high coverage sequencing, as demonstrated in the example embodiments.

Figure 4:
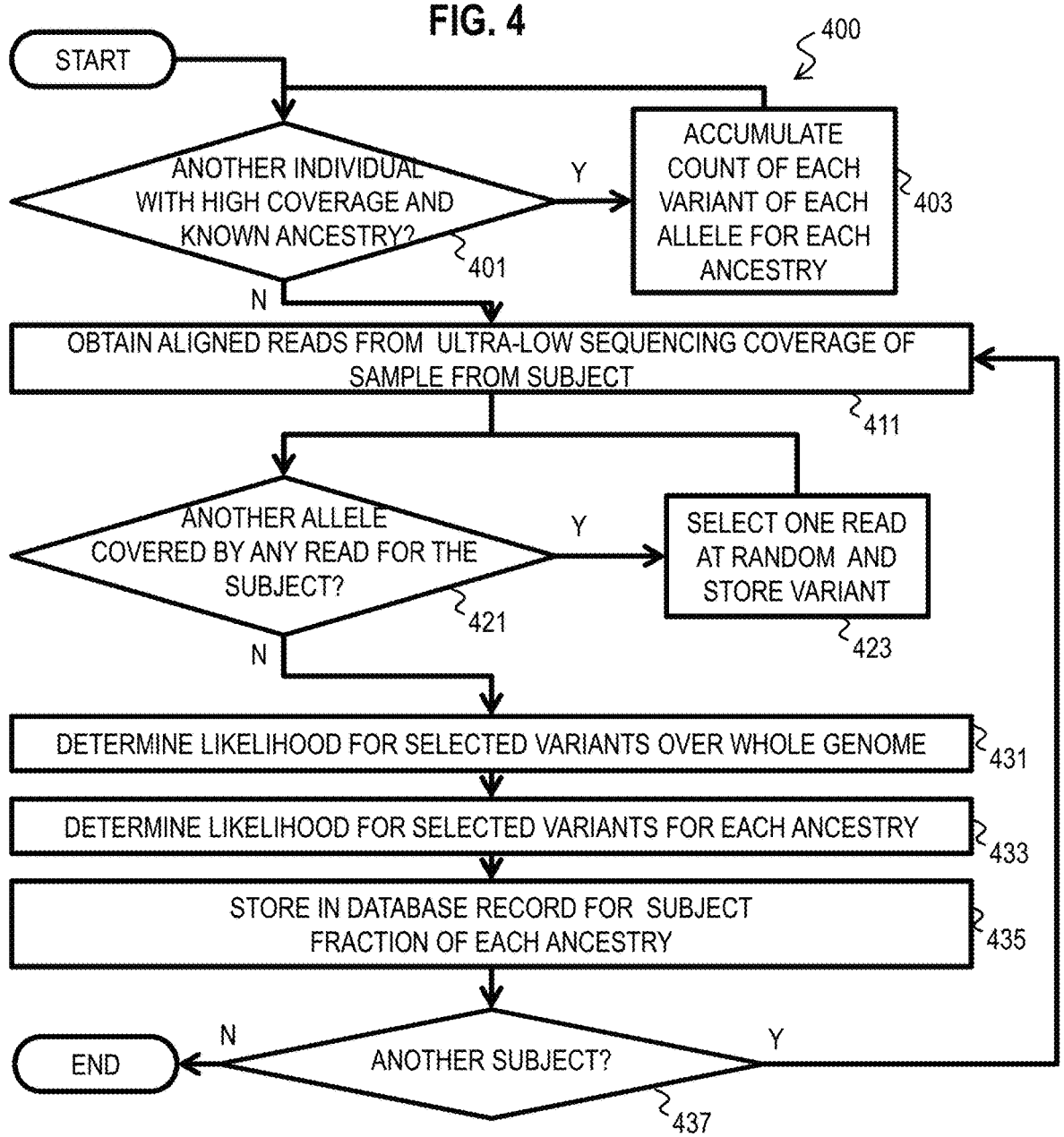
FIG. 4 is a flow diagram that illustrates an example method for determining ancestry based on aligned reads from ultra low coverage sequencing data, without imputing genotype, according to an embodiment.

FIG. 4 is a flow diagram that illustrates an example method 400 for determining ancestry based on aligned reads from ultra low coverage sequencing data, without imputing genotype, according to an embodiment. The method uses genotype information for individuals of known ancestry, such as available as published ethnic reference panels for European, African and Asian populations. It is expected that other ancestry reference panels will be published describing populations at high risks for certain diseases, such as sickle cell and Tay Sachs disease. A set of sequenced individuals of known ancestry is assembled to serve as references in ancestry analysis. For each population at each genetic variant a count of the reference allele and a count of the alternate allele were determined. These steps are represented in FIG. 4 as step 401 to determine if there is another individual in each known ancestry population, and if so, then in step 403, to accumulate counts for each variant of each allele. Since these steps need only be done once for each ancestry panel, they are considered to occur during step 303 in the method 300 of FIG. 3. The desired result is to identify the fraction of the subject's ancestry that comes from each of the reference populations and store that result in reference population field 242 of the ancestry results field 240.

In step 411 aligned reads from low coverage or ultra low converge sequencing are obtained for a subject. For example, this step is performed as step 311 in method 300 of FIG. 3. The following steps are performed as part of step 315 of method 300 in FIG. 3.

For each genetic variant covered by at least one sequencing read in the ultra-low-coverage sample, one sequencing read is randomly chosen, and which allele present is recorded. This is accomplished by step 421, which determines if there is another allele covered by any read for the subject stored in genotype data field 220. If so, then in step 423 one of the reads that cover that allele is selected at random and the variant for the randomly selected read is stored temporarily for subsequent processing.

In step 431, the likelihood for the selected variant within the reference genome is determined. For example, a statistical model like that used by Pritchard et al. is used. The Pritchard model is described on the World Wide Web at domain genetics of super domain org in subfolder 945 of subfolder 2 of subfolder 155 of folder content.

In step 433, the likelihood for the selected variants is determined for each ancestry. For example, the likelihood determined from step 431 is optimized using the SQUAREM algorithm available on the World Wide Web at subdomain onlinelibrary of domain wiley of super domain corn in subfolder abstract of subfolder/j.1467-9469.2007.00585.x of subfolder 10.1111 of folder doi.

In step 435, the output is then stored in the database 190, e.g., in fields 243 and 244, such that the values in the fields 244 for all populations add up to 1. In step 437 it is determined whether there is another subject for which to determine ancestry. Step 437 is performed, for example, during step 305 of method 300 in FIG. 3.

Thus, FIG. 4 depicts a method which includes determining a first likelihood for each variant in the plurality of aligned reads based on the target genome; determining a second likelihood for each variant based on a reference genome for a particular ancestry of a plurality of reference genomes for a corresponding plurality of ancestries; and determining a fraction of each ancestry of the plurality of ancestries based on the first likelihood and the second likelihood for a plurality of variants in the plurality of aligned reads.

Several of the next methods determine comparisons among sequence lengths in units of centimorgans (cM, $1M=10^{-2}$ Morgans) which measures genetic distance rather than physical distance between alleles. A centimorgan or map unit (m.u.), is defined as the distance between chromosome positions (also termed loci or markers) for which the expected average number of intervening chromosomal crossovers in a single generation is 0.01. (By inference the number of intervening chromosomal crossovers in a single generation is 1 for 1 Morgan, a unit rarely used in that denomination.) The number of base-pairs to which a centimorgan corresponds varies widely across the genome (different regions of a chromosome have different propensities towards crossover) and it also depends on whether the meiosis where the crossing-over takes place is a part of oogenesis (formation of female gametes) or spermatogenesis (formation of male gametes). One centimorgan corresponds to about 1 million base pairs in humans on average. It has been calculated that the female genome is 4782 centimorgans long, while the male genome is only 2809 centimorgans long.

Figure 5:
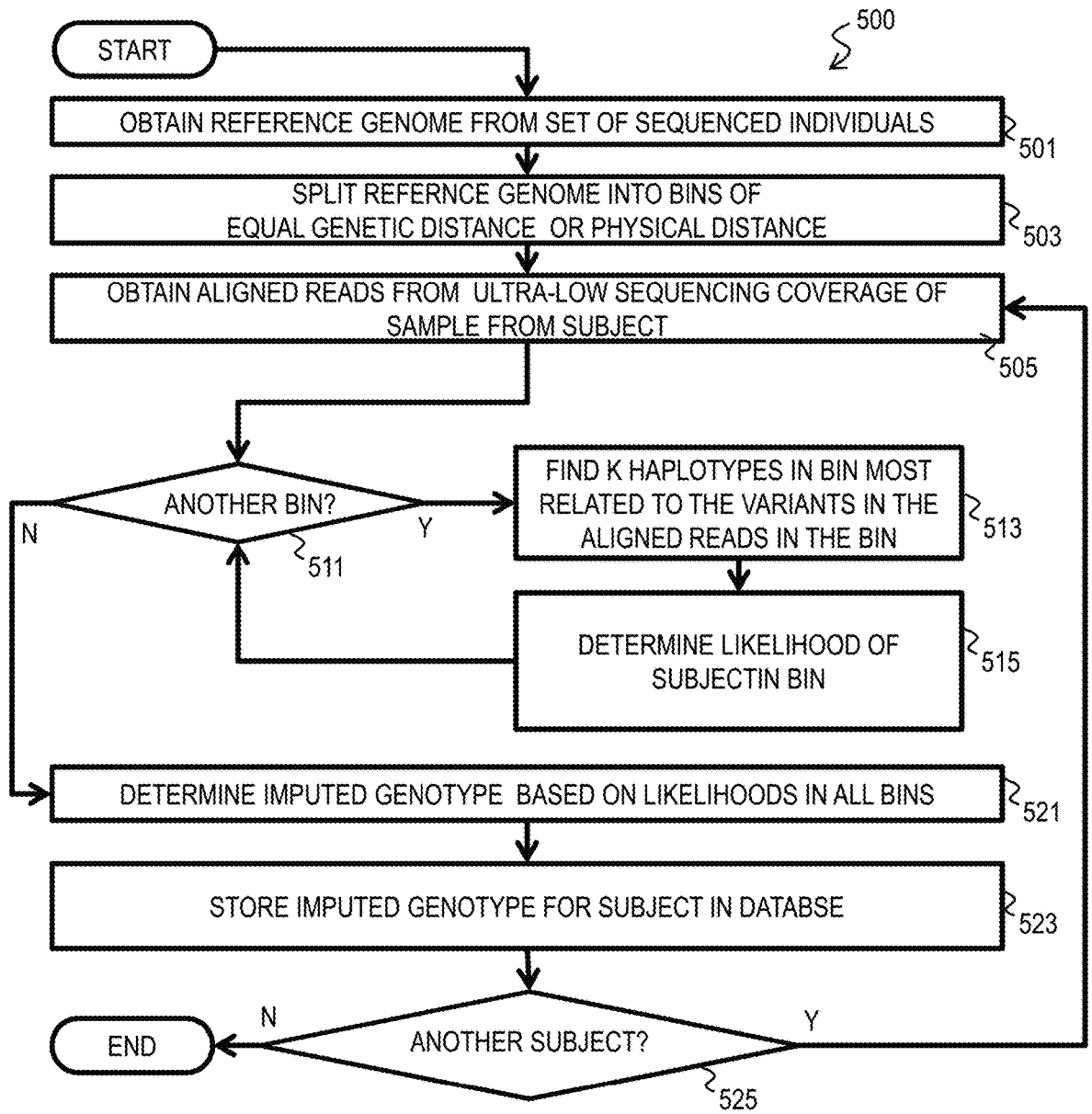
FIG. 5 is a flow diagram that illustrates an example method for imputing genotype based on aligned reads from ultra low coverage sequencing data, according to an embodiment.

FIG. 5 is a flow diagram that illustrates an example method 500 for imputing genotype based on aligned reads from ultra low coverage sequencing data, according to an embodiment. A set of sequenced individuals is used as an imputation reference panel. It is assumed that a subject is sequenced by ultra-low-coverage sequencing; and, the goal is to fill in the missing genotypes of the subject using the data from the reference panel. In step 501, a reference haplotype panel is obtained from a set of individuals subjected to whole genome sequencing. In step 503, the genome is split into bins, e.g., bins of 10 million base pairs. In some embodiments, bins of equal genetic distance, e.g., 10 cM are used. Since these steps need only be done once for each reference panel, steps 501 and 503 are considered to occur during step 303 in the method 300 of FIG. 3.

In step 505, aligned reads from low coverage or ultra low converge sequencing are obtained for a subject. For example, this step is performed as step 311 in method 300 of FIG. 3. The following steps are performed as part of step 317 of method 300 in FIG. 3.

In step 511, it is determined if there is another bin to process for the current subject. If so, control passes to step 513. If not, control passes to step 521. In step 513, for each bin, a set of K haplotypes is found in the reference panel that are most closely related to the variants observed in the subject. In step 515, a hidden Markov model (HMM), e.g., as proposed by Li and Stephens, is used to compute a likelihood of the observed genetic variants in the target individual. The HMM of Li and Stephens is found on the World Wide Web at subdomain ncbi of subdomain nlm of domain nih of super domain gov in subfolder 14704198 of folder pubmed. Control then passes back to step 511 to determine if there is another bin to process.

If there are no further bins to process, then in step 521, genotype imputation is performed in this HMM using the Baum-Welch algorithm described in the World Wide Web at subdomain en of domain Wikipedia of super domain org in folder wiki using file Baum%E2%80%93Welch_algorithm.

In step 523, the output is then stored in the database 190, e.g., in imputed genotype field 216. In step 525 it is determined whether there is another subject for which to determine imputed genotype. Step 525 is performed, for example, during step 305 of method 300 in FIG. 3.

Thus method 500 for analyzing one or more genetic samples includes procuring one or more genetic samples comprising genetic material from one or more individuals having a genotype, wherein each genetic sample is associated with the individual from which is was procured. The method includes sequencing the genetic material from each of the plurality of genetic samples using non-targeted, ultra-low coverage sequencing, wherein the ultra-low coverage is determined with reference to a target genome, to determine a plurality of genetic reads for each of the plurality of genetic samples, and wherein the genetic material is substantially non-ancient genetic material. The method also includes aligning the plurality of genetic reads obtained by sequencing each of the plurality of genetic samples to one or more reference genomes to produce plurality of aligned genetic reads for each of the plurality of genetic samples. The method also includes determining an imputed genotype of the individual by calculating a degree of similarity of the plurality of aligned genetic reads to each reference genome of the one or more reference genomes, and setting the reference genome with a highest degree of similarity as the imputed genotype; and assigning the individual to a genotypic or phenotypic group based on the imputed genotype.

Figure 6:
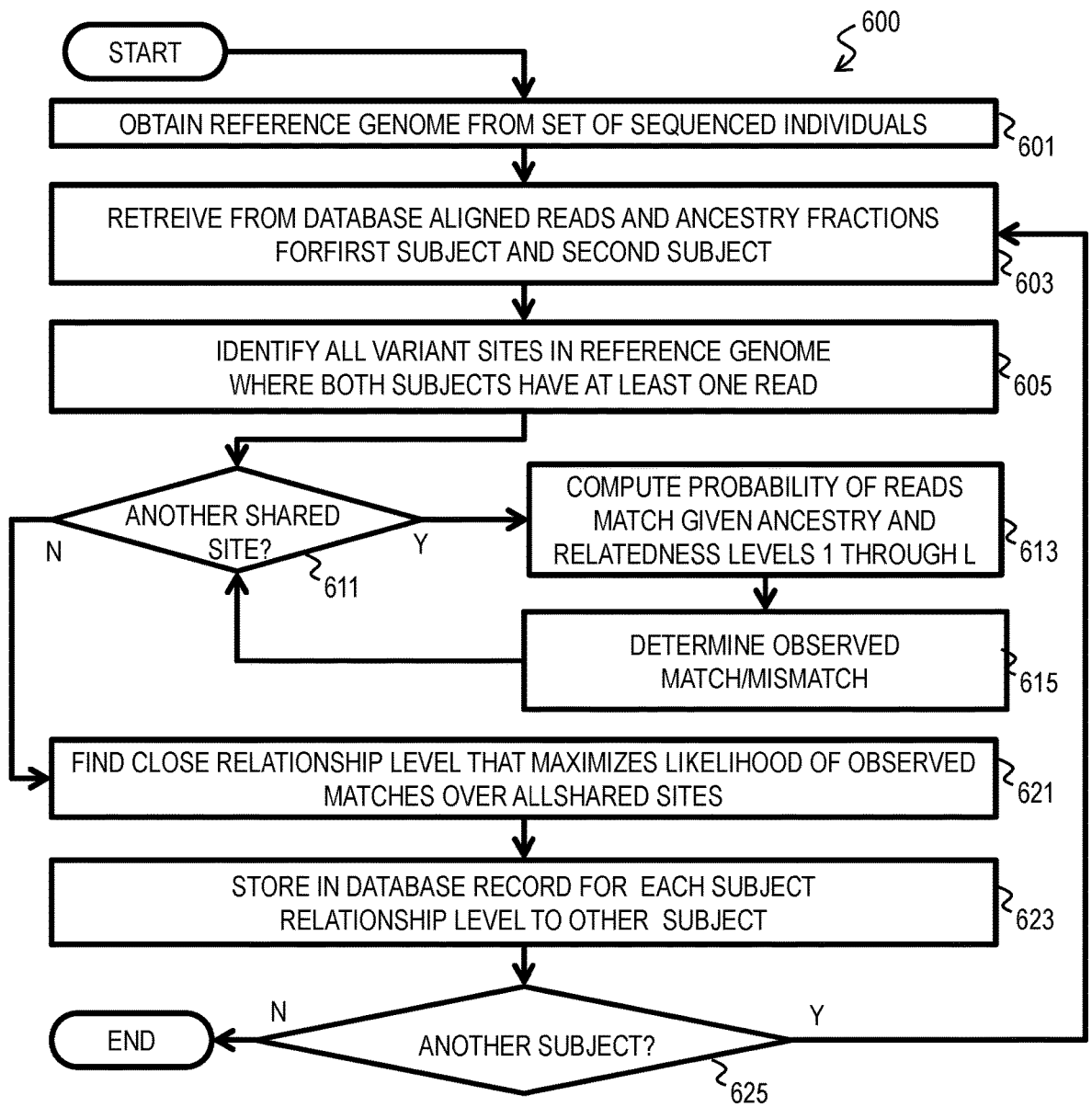
FIG. 6 is a flow diagram that illustrates an example method for determining close relatedness between two individuals based on aligned reads from ultra low coverage sequencing data, without imputing genotype, according to an embodiment.

FIG. 6 is a flow diagram that illustrates an example method 600 for determining close relatedness between two individuals based on aligned reads from ultra low coverage sequencing data without imputing genotype, according to an embodiment. In this analysis, two subjects who have ultra-low coverage sequencing data are compared to determine the extent to which they are related. The ancestry of both subjects are known by virtue of step 315 for the current subject and the results stored in ancestry results field 240 for both the current subject and the different subject.

In step 601, a reference haplotype panel is obtained from a set of individuals subjected to whole genome sequencing for each ancestry type used in step 315, described above. Since this step needs only be done once for each reference panel, step 601 is considered to occur during step 303 in the method 300 of FIG. 3.

In step 603, aligned reads from low coverage or ultra low converge sequencing are obtained for both the current subject and the different subject. For example, this step is performed as step 311 in method 300 of FIG. 3 for the current subject. In step 603 the aligned reads for the different subject are retrieved from the database. This part of step 603 is performed during step 323 of method 300 in FIG. 3. The next steps are performed during step 325 of method 300 in FIG. 3.

In step 605, all sites in the genome where both individuals have at least one sequencing read are identified. Each site is reviewed in the loop comprising steps 611, 613 and 615. In step 611 it is determined whether there is another site to review. If not, control passes to step 621, described below. Otherwise control passes to step 613.

In step 613, at the current site, the probability of a match between the reads in both individuals given the ancestry of the individuals and a certain relationship (e.g. siblings, cousins, etc.) is computed for relationships at least to level L, e.g., level 3. In step 615, the observed match is determined. The result of this is a true if the two subjects match or false if the two subjects to not match.

In step 621 a relationship level is determined that maximizes the likelihood of the observed matches and mismatches between the individuals. For example, if siblings are expected to match 25 percent of the time then a number of true observations that is approximately one third of the number of false observations is likely to indicate a sibling relationship, which is a relatedness level given by a relationship coefficient of 0.5.

In step 623, the output is then stored in the database 190, e.g., in relative field 252. In step 625 it is determined whether there is another different subject for which to determine relatedness. Step 625 is performed, for example, during step 321 of method 300 in FIG. 3.

This method 600 has been found to easily determine close relatives (up to around 3rd degree of relatedness, given by a relationship coefficient of 0.12, the level of first cousins). In summary, the method 600 for determining relatedness to a different individual includes automatically determining on a processor a first ancestry of the individual and second ancestry of the different individual. The method also includes automatically determining on a processor a first value of a variant from the plurality of aligned reads for the individual and a second value of the variant from a plurality of aligned reads for the different individual. The method also includes automatically determining on a processor likelihood that the first value matches the second value based on the first ancestry and the second ancestry and a level L of relatedness, for a plurality of values of L. The method also includes automatically determining on a processor an observed match has occurred if the first value matches the second value. The method also includes automatically determining on a processor a particular relatedness level that maximizes likelihood of observed match for each of a plurality of variants found in both the aligned reads of the individual and the aligned reads of the different individual.

Figure 7:
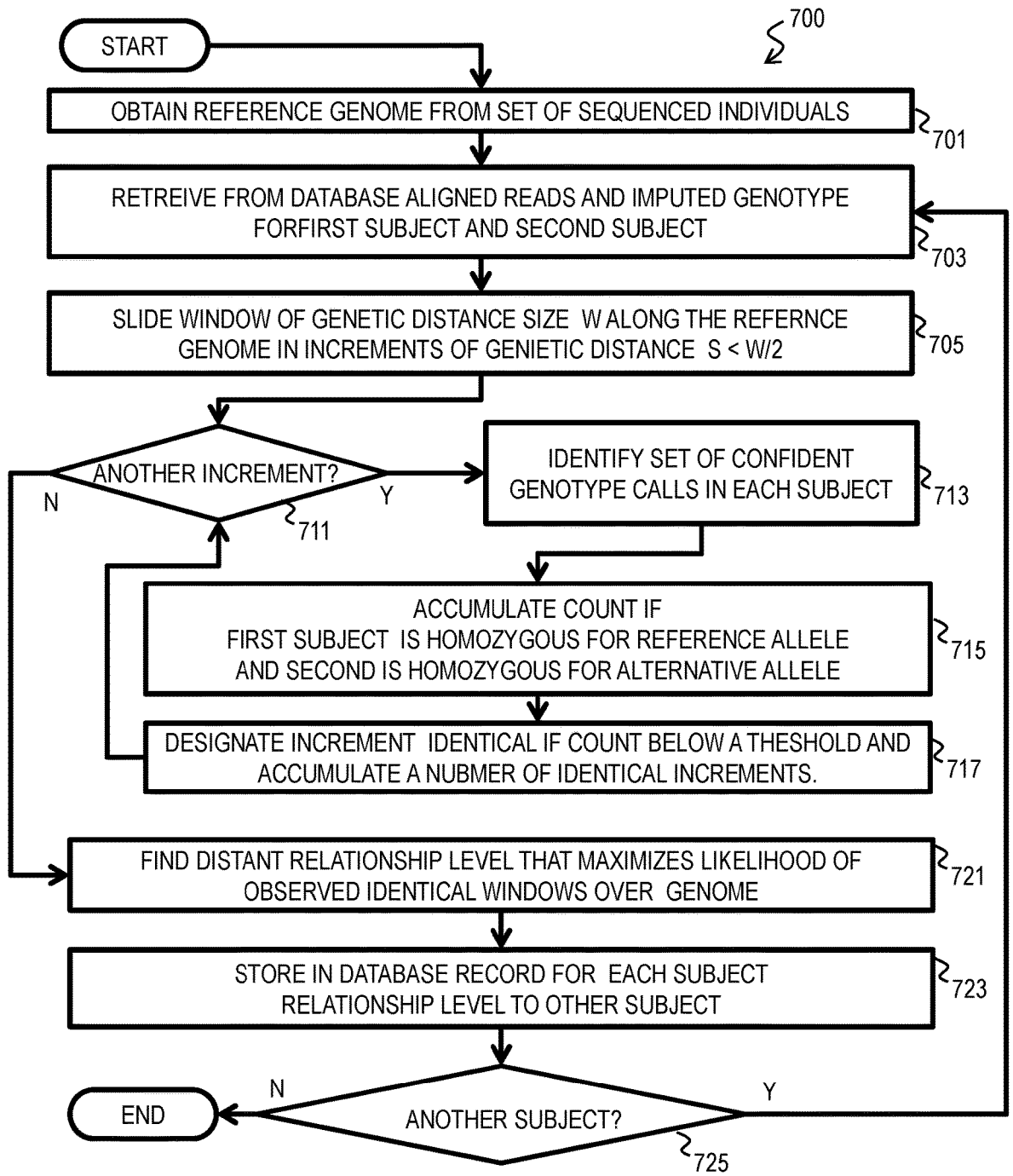
FIG. 7 is a flow diagram that illustrates an example method for determining distant or cryptic relatedness between two individuals based on aligned reads from ultra low coverage sequencing data, according to an embodiment.

FIG. 7 is a flow diagram that illustrates an example method 700 for determining distant or cryptic relatedness between two individuals based on aligned reads from ultra low coverage sequencing data, according to an embodiment. In this analysis, two subjects that have ultra-low coverage sequencing data are compared to determine the extent to which they are related, as in FIG. 6. However, method 700 is sensitive to more distant relationships, for example fourth cousins. Method 700 is based on identifying shared blocks of the genome. Relatives, even distant relatives, often share large parts of the genome in common; while, unrelated individuals do not. Method 700 starts from imputed genotypes placed into the database 190, such as field 216 of record 210, during step 317 of method 300 in FIG. 3, such as during step 523 of the method 500 in FIG. 5. Dissimilarity is measured by how many times the imputed genome of the two subjects have different variants of an allele. If two subjects are less dissimilar than expected at random, then the two subjects are more likely to be related. Using the method 700 depicted in FIG. 7, it is determined over how many portions of the genome the two subjects are less dissimilar than random. A level of relatedness is based on the number of portions that are less dissimilar than random.

In step 701, a reference haplotype panel or reference genome is obtained from a set of individuals subjected to whole genome sequencing. Since this step needs only be done once for each reference panel, step 701 is considered to occur during step 303 in the method 300 of FIG. 3. In step 703, aligned reads and imputed genotypes are retrieved from the database for both the current subject and the different subject. For example, step 703 is performed during step 323 of method 300 in FIG. 3. The next steps 705 through 721 are performed during step 325, along with, or instead of, the steps 605 through 623 of method 600 depicted in FIG. 6.

In step 705, a window of genetic distance size W (e.g., W is in a range from about 5 to about 10 centiMorgans, cM) is positioned along the reference haplotype panel or reference genome. The window is moved incrementally in genetic distance size increments of genetic distance S, such that S is less than W/2 (e.g., S is in a range from about 1 to about 4 cM). Thus, in step 705, a window of defined size in centiMorgans is made to slide along the reference panel or genome in increments.

In step 711, it is determined whether there is another increment left to which to slide the window. If not, control passes to step 721, described below. If there is yet another increment to slide the window, then control passes to step 713.

In step 713, thus at each increment, a set of confident genotype calls in both subjects is determined. For each imputed genotype there is a probability attached (e.g., the probability that this genotype is correct as called is 70% or 90% of alleles). For these purposes, a genotype call is "confident" if the estimated probability that it is correct is 95% or higher.

In step 715, accumulate a count of the set of confident genotype calls for which one subject is confidently homozygous for the reference allele and the other subject is confidently homozygous for the alternative allele. This count is a measure of dissimilarity. For example, if there is a single shared haplotype between the two subjects, then this count will be zero for the portion where the haplotype is shared, in the absence of any genotyping errors.

In step 717, it is determined whether the count for the increment is less than some threshold number that may account for sequencing or genotyping errors. If the count for the increment is less than the threshold, then call the two subjects identical for that increment. For example, call a segment as identical-by-descent if the count of opposite homozygote genotypes is below this threshold In some embodiments, step 717 includes accumulating the number of identical increments and the number of non-identical increments along the entire reference genome.

When there are no more increments, control passes from step 711 to step 721. In step 721, a distant relatedness level is determined based on the relatedness level (e.g., relationship coefficient) that maximizes the likelihood of the observed number of identical increments compared to non-identical increments. For example, a method can be used as described by Huff, at the World Wide Web at subdomain ncbi of subdomain nlm of domain nih at super domain gov, in file PMC3083094 of subfolder articles of folder pmc, the entire contents of which are hereby incorporated by reference as if fully set forth herein, except for terminology inconsistent with that used herein.

In step 723, the output is then stored in the database 190, e.g., in relative field 252. In step 725 it is determined whether there is another different subject for which to determine relatedness. Step 725 is performed, for example, during step 321 of method 300 in FIG. 3.

This method 700 has been found to easily determine distant relatives or cryptic relatedness (up to around 5th degree, L=5, relatedness. Thus, the method 700 for identifying cryptic ancestral relatedness between at least two genetic samples includes determining a first imputed genotype and first plurality of aligned reads for a first genetic sample, and determining a second imputed genotype and second plurality of aligned reads for a second genetic sample. The method also includes comparing the first and second imputed genomes in each of a plurality of windows of genetic distance D to produce a count that is incremented when the first genetic sample is homozygous for a first variant value in the window and the second genetic sample is homozygous for alternative variant value in the window.

The method also includes designating the window identical, if the count for the window is less than a threshold count. The method also includes determining a relatedness level that maximizes a likelihood of an observed number of identical windows.

EXAMPLES

Examples are provided below to facilitate a more complete understanding. The following examples illustrate the example modes of making and practicing various embodiments. However, the scope of the invention is not limited to specific embodiments disclosed in these Examples, which are illustrative only, since alternative methods can be utilized to obtain similar results.

Example 1—High Throughput Extraction of Genomic DNA from Saliva and Library Preparation DNA Extraction and Purification (Method 1).
Cell Lysis.

For cell lysis, saliva was collected from multiple individuals in a Spectrum DNA saliva collection tube, and cell lysis was carried out as follows: Saliva collection tubes were vortexed until contents were properly resuspended, and 138 μl of resuspended saliva was aliquotted into each well of a 96 well plate (200 ul holding capacity). A reaction master mix was prepared (36 μl 5M NaCl (from Ambion of city, state); 4.5 μl 1M MgCl2 (from Sigma of city, state); 1.8 μl Express extract buffer (from Kapa of city, state); 0.36 μl Express extract enzyme (from Kapa). 42 μl of the master mix were aliquotted into each of the wells, and the contents were mixed using a multi-channel pipette. The total volume of each reaction was 180 μl. The plate was sealed with Bio-rad seal and incubated at 75° C. for 30 min, 95° C. for 5 min, then at 4° C. hold in a thermocycler. After this incubation, the plate was spun for 10 minutes (min) at 2400 g.

DNA Purification.

For DNA purification, the following master mix was prepared: 40 μl 10×TEC Binding buffer (1 M NaOAc (from Ambion), 1 M NaCl (from Ambion), 0.1% Tween-20 (from Enzo Life Sciences of city, state); pH 4) and 15 μl histamine modified TEC Beads (hereinafter, "TEC beads") for each DNA purification reaction. 55 μl of this master mix was aliquotted into each well of a fresh 96 well plate (each well has a 500 ul holding capacity). 200 μl of pure isopropanol (from Amresco of city, state) was added to each well, followed by 145 μl of supernatant from the cell lysis step above. The contents of each well were mixed and incubated at room temperature for 5 min. Note: at this step the beads sometimes became sticky and behaved differently depending on the amount of genomic DNA in the well; the more DNA, the stickier and clumpier the beads would get. In this situation, the reaction mix was pipetted up and down at least 5 times to suspend the beads. However, if the beads did not suspended properly, that did not seem to affect the subsequent reaction.

The plate was placed on a magnetic stand to move beads out of suspension until the supernatants were clear. The supernatants were then discarded, and the beads washed twice with 450 μl of high salt TEC Wash Buffer (10 milliMolar (mM, 1 mM=$10^{-3}$ Molar) sodium phosphate, 500 mM NaCl, 0.01% Tween-20, pH 6.0), and once with no salt TEC Wash Buffer (10 mM sodium phosphate, 0.01% Tween-20, pH 6.0). For each wash, the respective buffer was added to the beads and mixed until the beads were resuspended. As mentioned above, the beads may be sticky and clumpy; if so, the beads were resuspended as much as possible. The plate was then placed on a magnetic stand until the supernatants were clear, and the supernatants were discarded. 15 μl of TEC Elution Buffer (10 mM Tris.HCl, pH 8.5, 0.01% Tween-20) was added and the beads resuspended. (At this step, the beads should resuspended properly without stickiness or clumping.) The plate was incubated at 55° C. for 2 min on a thermo mixer. After the incubation, the plate was placed on a magnetic stand until the supernatants were clear, and each supernatant (eluate) was loaded into a fresh 96 well plate. The TEC bead nucleic acid isolation technology, including the preparation of the TEC beads and various buffers used, is disclosed in U.S. patent application Ser. No. 15/097,781 filed on Apr. 13, 2016, the entire disclosure of which is herein incorporated by reference.

DNA Extraction and Purification (Method 2).
Cell Lysis.

For cell lysis, saliva was collected from multiple individuals in a Spectrum DNA saliva collection tube, and cell lysis was carried out as follows: Saliva collection tubes were vortexed until contents were properly resuspended, and 40 μl (or any other desired volume) of resuspended saliva was aliquotted into each well of a 96 well plate (200 μl holding capacity). The plate was incubated at 50° C. for 1 hour to lyse the cells and denature proteins.

DNA Purification.

For DNA purification, the following master mix was prepared: 17 μl (or any other volume representing ~2:3 ratio of buffer to saliva) "Bind 1" buffer (AGENCOURT® DNAdvance™, A48706 from Beckman Coulter, of city, state) or buffer comprising of 20% PEG and 2.5 M NaCl and 28.5 μl (or any other volume representing of ~1:4 ratio of bead suspension to saliva), "Bind 2" bead suspension, or Agencourt AMPure XP beads (A63882 from Beckman Coulter), or SPRIselect beads (B23319 from Beckman Coulter). The contents of each well were mixed and incubated at room temperature for 5 min, and the plate was placed on a magnetic stand until the supernatants were clear. The supernatants were then discarded, and the beads washed three times with 70% EtOH. During each wash, the beads were thoroughly resuspended by pipetting up and down and the supernatant was discarded after each wash. After the last wash, the supernatant was discarded and the beads were immediately resuspended in 20 μl of TE buffer (10 mM Tris, 1 mM EDTA, pH 8.0) or nuclease-free water to elute the DNA.

DNA Normalization.

DNA obtained from either Method 1 or Method 2 was normalized prior to sequencing as follows. The entire plate was quantified using Quant-iT picoGreen dsDNA Assay kit, using use 1 or 2 μl from each well for measurement. Approximately 10 samples were chosen based on picogreen fluorescence to represent the whole range of values, concentrations were measured with a Qubit dsDNA High sensitivity assay kit using 1 μl of each sample for measurement. A normalization curve was built using Qubit values, and the values for other samples were extrapolated. A Mantis robotic liquid handler was used normalize an aliquot of each elute to ~0.2 nanograms per microliter (ng/μl, 1 ng=$10^{-9}$ grams).

Library Preparation and Normalization Before Sequencing.
Library Preparation.

A DNA library was prepared using the Nextera XT DNA library prep Kit from Illumina. Using the manufacturer's protocol, low-volume Nextera reactions were performed; e.g., approximately $\frac{1}{8}^{th}$ of the volume of each of the components normally used, with on average 0.2 ng/μl DNA (in practice, 0.15-0.23 ng/µl DNA). Note: Nextera kits seem to be variable in terms of how much transposase is present, so each box was tested on the same DNA sample in order to adjust the DNA concentration to the transposase concentration. A Mantis robotic liquid handler (from Formulatrix, Inc., of Bedford, Mass.) and a Bravo robotic liquid handler (from Agilent Technologies, of Santa Clara, Calif.) were used to set up the reactions. Barcoded primers were ordered from Illumina.

12 cycles were used for DNA amplification, and the samples were purified as follows: 6 µl of amplified DNA was transferred from each well of the PCR plate and 3 µl TEC beads were added (0.6×) with 1 µl of 10×TEC Binding Buffer (pH 4) and 1µ of water for total of ~10 µl and mixed well. (The water was used because slight evaporation occurs during PCR.) The plate was placed on a magnetic table until the supernatants were clear, and the supernatants were discarded. The beads were washed three times with 150 µl of 250 mM salt TEC Wash Buffer, and once with 150 µl of no salt TEC Wash Buffer, the beads were recovered as above and all supernatants discarded. The DNA was eluted in 12 µl TEC Elution Buffer, and the elutes were transferred into a 96 well plate of 200 µl holding capacity.

Alternatively, 12 cycles were used for DNA amplification, and the samples were purified as follows: a mastermix of 14 µl of water and 10 µl of Agencourt AMPure XP beads (A63882 from Beckman Coulter), or SPRIselect beads (B23319 from Beckman Coulter) were added to each library, mixed well and incubated for 5 min at room temperature. The plate was placed on a magnetic stand until the supernatants were clear. The supernatants were then discarded, and the beads washed twice with 70% EtOH without removing the magnet or disturbing the beads. After the second wash the beads were dried at room temperature for 2 min and resuspended in 20 µl of TE buffer (10 mM Tris, 1 mM EDTA, pH 8.0) or nuclease-free water to elute the DNA.

Normalization Before Sequencing.

The entire plate was quantified using Quant-iT picoGreen dsDNA Assay kit. Approximately 10 samples were chosen based on picogreen fluorescence to represent the whole range of values, concentrations were measured with a Qubit dsDNA High sensitivity assay kit using 1 µl of each sample for measurement. A normalization curve was built using Qubit values, and the values for other samples were extrapolated. If the concentration values of the samples were negative, then the sample was not included for sequencing. Based on the quantitation, an appropriate amount of each sample was pooled so there was enough DNA to sequence, typically 10 µl of 2 nanoMolar (nM, 1 nM=$10^{-9}$ Molar) sample was used for each lane. Equation 1 was used to back-calculate the DNA mass needed for sequencing. To determine the concentration of the library:

$$\text{Concentration (in nM)} = \text{concentration (in ng/ul)} * 10^6 / (660 * \text{average size of library (in bp)}) \quad (1)$$

The pooled sample was concentrated using TEC beads. For example, if the total volume after pooling is 100 µl, then the following reaction was set up: 100 µl sample; 10 µl TEC beads; 12.5 µl 10×TEC Binding Buffer; and 2.5 µl water, for a total of 125 µl. After binding, the supernatant was discarded. The beads were then washed once with no salt wash buffer. To concentrate the DNA, the TEC beads were allowed to bind the DNA, the beads were recovered, and the supernatant discarded. The samples were spun and the last amounts of final wash buffer were removed. The DNA bound to the TEC beads was eluted in 14 µl of TEC Elution Buffer. The concentration of the recovered DNA was determined using Qubit and run on a bioanalyzer for size distribution. The molarity of each DNA sample was calculated, and the samples sent for sequencing.

Alternatively, the pooled sample was concentrated using SPRI beads. Sixty microliters (or any other suitable volume) of the pooled library was mixed with 0.55× ratio of SPRI beads (A63882 from Beckman Coulter), or SPRIselect beads (B23319 from Beckman Coulter). The beads were added to the pooled libraries, mixed well and incubated for 5 min at room temperature. The plate was placed on a magnetic stand until the supernatant was clear. The supernatant was then discarded, and the beads washed twice with 70% EtOH without removing the magnet or disturbing the beads. After the second wash the beads were dried at room temperature for 2 min and resuspended in 20 µl of TE buffer (10 mM Tris, 1 mM EDTA, pH 8.0) or nuclease-free water to elute the DNA. The concentration of the recovered DNA was determined using Qubit and run on a bioanalyzer for size distribution. The molarity of each DNA sample was calculated, and the samples sent for sequencing.

Example 2—Ultra-Low-Coverage Sequencing and Ancestry Analysis from Human DNA Samples Thirteen DNA samples corresponding to individuals who participated in the 1000 Genomes Project were obtained from the Coriell Institute for Medical Research (see Table 1 below). In Table 1, the "Identifier" column is the individual identifier from the Coriell Institute for Biomedical Research, and the "Population" column is the population code from the 1000 Genomes Project. Individuals with the labels ACB and AFR are of admixed African and European ancestry (African-Americans or Afro-Caribbean individuals), individuals with the labels CEU, GBR, IBS, and TSI are of European ancestry (from either northern or southern Europe), and individuals with the labels MXL and PUR are of Hispanic ancestry (from Mexico or Puerto Rico).

TABLE 1

DNA samples used in Example 2

| Identifier | Population |
|---|---|
| HG02332 | ACB |
| HG02282 | ACB |
| HG02282 | ACB |
| NA19700 | AFR |
| NA07357 | CEU |
| HG00118 | GBR |
| HG01630 | IBS |
| HG01522 | IBS |
| NA19649 | MXL |
| NA19670 | MXL |
| NA19671 | MXL |
| HG01170 | PUR |
| NA20502 | TSI |

As described above in Example 1, the DNA concentration for each sample was quantified using the Quant-iT picoGreen dsDNA Assay, and an aliquot was taken from each sample and normalized to a concentration of 0.15 ng/µl. Sequencing libraries were made from each sample using the Nextera XT DNA library prep Kit from Illumina, as described above in Example 1. At all steps of the manufacturer's protocol, all volumes were reduced by a factor of eight. Barcoded primers obtained from Illumina were used.

After the Nextera library prep reaction, DNA was purified. The purification reaction for each sample included 6 µl of the DNA input, 3 µl of TEC Beads, 1 µl of 10×TEC Binding Buffer, and 1 µl of water. The samples were placed on a magnetic plate and the supernatant removed. The beads were washed three times with 150 µl of 250 mM salt TEC Wash Buffer 10 mM sodium phosphate, 250 mM NaCl, 0.01% Tween-20, pH 4.5 or 5.0) and once with 150 µl of no salt TEC Wash Buffer. The DNA was eluted in 12 µl TEC elution buffer and transferred into a 96 well plate of 200 µl holding capacity. For each sample, the concentration of the library was obtained using Quant-iT picoGreen dsDNA Assay kit. DNA from each sample was concentrated to obtain a 2 nM solution in 10 µl. The libraries were run on a bioanalyzer to obtain their size distributions, pooled and sequenced on an Illumina MiSeq. Sequencing results were obtained in FASTQ format and de-multiplexed so that a single FASTQ file corresponded to a single barcoded sample.

Sequencing reads were aligned to the human genome reference hg19 using the bwa-mem algorithm (arXiv: 1303.3997) available online through the Cornell University Library. A reference set of known variable sites were obtained from the 1000 Genomes Project, Phase 3. For each sample, the number of sequencing reads in each sample covering at least one site was counted. This number varied across samples from 568,126 to 6,410,352; since there are about 80 million variants in the 1000 Genomes Project, Phase 3 release, this corresponds to an effective genomic coverage per sample of 0.008× to 0.08×. For each sample at each known variable position, a single read covering the position (if there was at least one) was sampled and the value (nucleotide base) of the read recorded. These reads were merged with the 1000 Genomes Phase 3 data. Principal component analysis was performed on individuals labeled as "YRI" (Yoruba from Nigeria), "CEU" (individuals of Northern European ancestry living in Utah) and "CHB" (Han Chinese individuals) to define the first two principal components. The remainder of the 1000 Genomes samples and the test samples were projected on to these principal components using smartpca version 13050, as described in Price et al. (2006), Principal components analysis corrects for stratification in genome-wide association studies, Nature Genetics 38, 904-909. For this smartpca run, the 1sqproject option was set to TRUE.

The ancestry of each individual was then obtained by visual inspection of their clustering in PCA space (see FIG. 3). The ultra-low-coverage sequencing samples of African ancestry cluster with the individuals of known African ancestry, and the same is true for the individuals of European or Latino ancestry.

Example 3—Ultra-Low-Coverage Sequencing for Genome-Wide Genotyping Using Genotype Imputation Sequencing read data from ultra-low-coverage sequencing of 13 DNA samples was obtained from Example 2. A reference set of known variable sites were obtained from the 1000 Genomes Project, Phase 3. For each of the known variable sites covered by at least one sequencing read, a genotype likelihood was calculated for each sample, corresponding to the probability of each true genotype given the observed sequencing reads. A version of the 1000 Genomes reference panel was created that excluded the individuals who were sequenced at ultra-low-depth. Imputation from the genotype likelihoods was performed using the software BEAGLE (see Browning B L and Yu Z (2009), Simultaneous genotype calling and haplotype phasing improves genotype accuracy and reduces false-positive associations for genome-wide association studies, Am J Hum Genet. 85(6): 847-61) and this modified 1000 Genomes Project, Phase 3 reference panel. A set of genetic variants with high predicted imputation quality ($r^2 > 0.8$ for the predicted correlation between the true allelic dosage and the imputed allelic dosage) were extracted from the output. The number of such genetic variants was 3,977,666.

Figure 10:
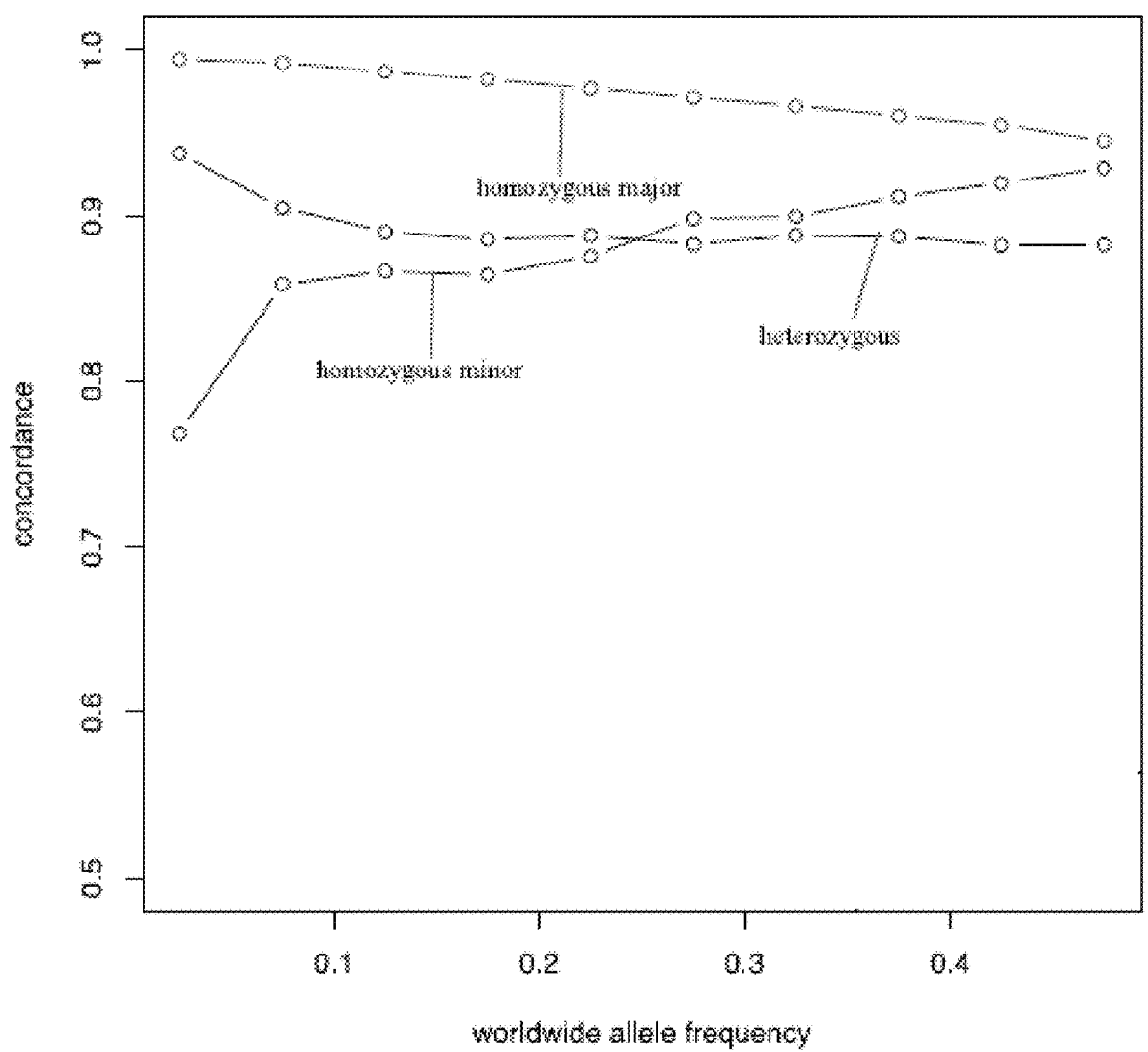
FIG. 10 is a graph showing the concordance between imputed genotypes from an individual sequenced to 0.08× coverage and whole genotype sequencing results. Results are calculated in different bins of worldwide allele frequency.

To estimate the accuracy of this imputation, imputed genotypes were compared to the known genotypes from the 1000 Genomes Project. For each sample, concordance between the imputed genotypes and sequences from the 1000 Genomes Project were computed separately in different bins of worldwide allele frequency, and separately depending on the genotype call (homozygous only for the minor allele, and either heterozygous or homozygous for the major allele) on the sample from the 1000 Genomes Project. Concordance for alleles of a certain frequency is the fraction (or percent) common to both the known genotype and to the sample imputed to the genotype based on ultra low coverage. In some embodiments, the fraction for each frequency is determined using the imputed genotypes where no sequencing data is present. FIG. 10 shows these concordances for a sample of an individual from Great Britain sequenced to about an 0.08× sequencing depth. Even for known heterozygous sites, concordance remains around 90%, despite the fact that most sites are covered by only a single sequencing read.

Example 4—Ultra-Low-Coverage Sequencing and Ancestry Analysis from Human Saliva Samples Saliva samples were obtained from 54 human individuals. Some individuals provided two samples, one from spitting into a Spectrum DNA saliva collection tube, and one from using a swab kit. In total 96 samples were obtained. For each sample, cells were lysed in a reaction mix of 36 µl of 5M NaCl, 4.5 µl of 1M MgCl2, 1.8 µl of Express extract buffer, and 0.36 µl of Express extract enzyme, along with 138 µl of saliva with incubation at 75° C. for 30 min and 95° C. for 5 min. This was performed in a 96 well plate. After the incubation, the plate was spun for 10 min at 2400 g.

DNA was extracted from the lysed cells as follows. 145 µl of the supernatant from step 1 was mixed with 200 µl of pure isopropanol, 15 µL of TEC beads, and 40 µl of 10×TEC Binding Buffer. This mix was incubated for 5 min at room temperature. The 96 well plate was placed on a magnetic stand until the supernatant was clear, and then the supernatant was discarded. The beads were washed twice with 450 µl of 500 mM TEC Wash Buffer and once with no salt TEC Wash Buffer. Beads were then resuspended in 15 µl of TEC elution buffer and incubated at 55 C for two minutes. The 96 well plate was then placed on a magnetic stand until the supernatant was clear, and the supernatant transferred to a separate 96 well plate.

Sequencing libraries were prepared from the eluted DNA as described in Example 2. The sequencing libraries were pooled and sequenced on four lanes of an Illumina HiSeq2500. Sequencing results were obtained in FASTQ format and de-multiplexed so that a single FASTQ file corresponded to a single barcoded sample. Sequencing reads were aligned to the human reference genome hg19 using the bwa-mem algorithm (arXiv:1303.3997) available online through the Cornell University Library. A reference set of known variable sites were obtained from the 1000 Genomes Project, Phase 3. For each sample, the number of sequencing reads covering the site in each sample was counted. After excluding four samples with effectively no coverage, this number varied across samples from 2,931,807 to 32,045,558, corresponding to an effective genome coverage of 0.04× to 0.4×.

Figure 11:
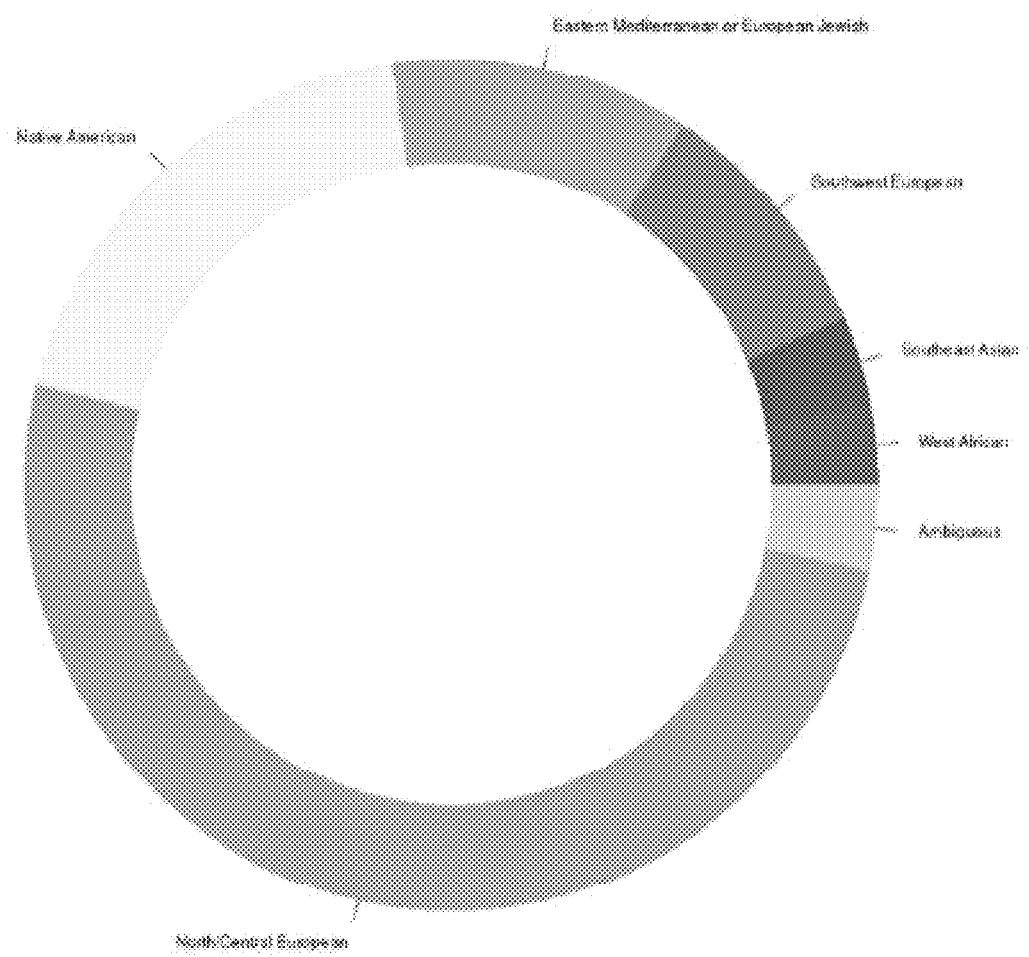
FIG. 11 is a diagram showing ancestry analysis from the ultra-low-coverage sequencing of an individual of self-reported mixed ancestry, using an example embodiment of the method.

We estimated sample cross-contamination by counting the numbers of reads mapping to mitochondrial DNA and identifying samples with evidence for multiple mitochondria, as judged by having polymorphisms within the sample. The ancestry of each individual was estimated as described above with reference to FIG. 4, which allows for individuals to have mixtures of ancestries, implements the statistical model described in Pritchard J K et al. (2000), Inference of population structure using multilocus genotype data Genetics. 2000 June; 155(2):945-959, the entire disclosure of which is incorporated herein by reference. In the ancestry algorithm, the user can provide genotypes from a set of labeled individuals of known ancestry and genotypes from a test individual of unknown ancestry. In this Example, a set of labeled genotypes was assembled from public sources. For a given set of mixture fractions (for example, if the test individual is assumed to have 50% of their ancestry from population 1 and 50% from population 2), the likelihood of the data can be computed using the likelihood function from the "admixture" model from Pritchard et al. (2000), supra. The ancestry algorithm uses the expectation-maximization algorithm to optimize the mixture proportions of each test individual. The ancestry algorithm was run 10 different times by randomly sampling 100,000 known polymorphic sites, and these runs summarized by identifying the ancestral components that were consistent across runs. The output of this algorithm is an estimated fraction of an individual's ancestors that came from different ancestral groups. An example from an individual who self-identified as of "Mixed Native American and European" ancestry is shown in FIG. 11.

Example 5—Microbiome/Food Analysis from Ultra-Low-Coverage Sequencing of a Human Saliva Sample Sequencing reads derived from ultra-low-coverage sequencing of a single individual were obtained from Example 4. Reads were mapped against the human genome hg19, and then a FASTQ file created containing all of the sequencing reads that did not match the human genome. A reference dataset of FASTA files corresponding to the NCBI Nucleotide database was downloaded and indexed using the software package Kraken (see Wood D E and Salzburg S L (2014), Kraken: ultrafast metagenomic sequence classification using exact alignments, Genome Biology 15:R46), which was used to match the non-human sequencing reads to the NCBI Nucleotide database. Read matches were then filtered using "kraken-filter" with a setting of 0.2, and the summaries created using "kraken-report." The numbers of sequencing reads matching different taxa were summarized at different taxonomic levels. Table 2 shows quantifications of select taxa identified in this sample. The sequence composition is consistent with the source of the sample as a human mouth.

TABLE 2

Quantifications of Select Taxa Identified

| Taxonomic level | Taxon name | Number of sequencing reads |
| --- | --- | --- |
| Bacteria-Phylum | Proteobacteria | 30,981 |
| Bacteria-Phylum | Firmicutes | 22,549 |

TABLE 2-continued

Quantifications of Select Taxa Identified

| Taxonomic level | Taxon name | Number of sequencing reads |
| --- | --- | --- |
| Bacteria-Phylum | Actinobacteria | 909 |
| Bacteria-Phylum | Bacteroidetes | 752 |
| Bacteria-Phylum | Fusobacteria | 336 |
| Virus-Family | Podoviridae | 40 |
| Virus-Family | Siphoviridae | 17 |
| Virus-Family | Myoviridae | 13 |
| Eukaryote-Species | *Triticum aestivum* | 14 |

Example 6—Ultra-Low-Coverage Sequencing to Test for an Association Between Genetic Variants and a Trait without Genotype Imputation Mapped sequencing reads for a set of individuals of known eye color were obtained from Example 4. For each individual, all sequencing coverage in the region of 27-30 Mb on human chromosome 15 was extracted. This region was chosen because it is known to contribute to human eye color variation. Individuals were split into groups according to whether they reported their eye color as "blue"/"light" or "brown"/"black". Then for each individual in each group, at each position in the genome, a single sequencing read covering the position was sampled (if there was at least one). All sites in this region of the genome that were polymorphic in this set of individuals were identified without using a known set of polymorphisms (note that this procedure discovers both common and rare variants). For each of these sites, the frequency of each of the genetic variants was calculated separately in the set of individuals with blue and brown eyes, and a P-value for a difference in the groups was calculated using Fisher's exact test.

The known genetic variant was recovered at position 28,365,618, where some chromosomes carry a G and some carry an A. The frequency of G was 100% among the individuals with blue eyes (5/5 chromosomes in this population carried the G allele) and at 28% frequency among individuals with brown or black eyes (2/7 chromosomes carried the G allele). By Fisher's exact test, the P-value for a difference in frequency between these groups was 0.028, consistent with the known association between this genetic variant and blue eye color.

Example 7—Identification of Related Individuals from Ultra-Low-Coverage Sequencing Mapped reads that cover known polymorphic sites in the human genome were obtained from Example 2. Two of these individuals (NA19671 and NA19670) are a father-child pair. The site of polymorphic sites covered by at least one sequencing read in both NA19670 and NA19671 was identified, a single sequencing read from each sampled, and the value (nucleotide base) at the site recorded. Each site was additionally labeled according to its allele frequency in the entire 1000 Genome Phase 3 dataset. The set of polymorphic sites with a minor allele frequency between 1% and 10% was then extracted. From these sites, the set of sites where the sampled allele from NA19671 matched the known minor allele was extracted, and the concordance between the allele in NA19670 and NA19671 was examined. Since these two individuals are a father-child pair, a random rare allele sampled from each of these individuals should match 50% of the time. There were 225 sites covered in both individuals where NA19671 carried the minor allele. Of these, NA19670 and NA19671 were a match at 102 (45%+/−7%), consistent with the known relationship.

To test whether this level of matching was specific to the father-child pair, we performed the same concordance analysis done for NA19671 with the other individuals. The results are shown in Table 3. Informative sites are sites that are covered by at least one sequencing read in both the test individual and NA19671 have an allele frequency between 1% and 10% in the 1000 Genomes Phase 3 data, and where NA19671 matches the minor allele. The true child of NA19671 has the highest match percentage of all individuals tested.

TABLE 3

Identification of relatives of NA19671.

| Identifier | # informative sites | # matching sites | Fraction matching |
|---|---|---|---|
| HG00118 | 850 | 129 | 0.15 |
| NA20502 | 789 | 132 | 0.17 |
| NA07357 | 726 | 122 | 0.17 |
| HG01522 | 761 | 131 | 0.17 |
| HG02282 | 399 | 91 | 0.23 |
| HG02332 | 306 | 70 | 0.23 |
| HG01170 | 122 | 31 | 0.25 |
| HG01630 | 310 | 84 | 0.27 |
| HG01881 | 305 | 91 | 0.29 |
| NA19649 | 121 | 44 | 0.36 |
| NA19700 | 89 | 34 | 0.38 |
| NA19670 | 225 | 102 | 0.45 |

Example 8—Performance Relative to Targeted and High Coverage Sequencing Data

One standard metric for the performance of a genome-wide genotyping or sequencing technology is the squared correlation of the measurements to the truth (the $r^2$ metric, also called the $r^2$ metric). For example, a set of N individuals and M known genotypes is assumed. Using a genotyping array or a sequencing assay and employing genotype imputation to fill in any missing data, determine inferred genotypes for the N individuals based on N samples, one from each individual. Then, the inferred genotypes for those N individuals are compared to the true genotypes for those N individuals. For each variant, the squared correlation coefficient of the inferred to true genotypes across all N individuals is determined for each of M genotypes. These M squared correlation coefficient values are then averaged to get an average measure of the accuracy of the technology. In practice, these squared correlation coefficient values are usually measured in bins of variants of different frequencies, since it is harder to accurately call rare variants as compared to common ones.

Two standard, inexpensive genotyping arrays (the Illumina CoreExome array and the Illumina Global Screening Array) were compared to ultra-low-coverage sequencing. To do this, the public 1000 Genomes data was used. Half of the data was used for simulations of both truth and observations, and the other half were used as an imputation reference panel. For each test sample, the variants that are genotyped on the array were extracted, and imputation was performed using the reference panel. A 0.2× and a 0.4× low coverage sequencing were simulated, and imputation performed using the reference panel. The $r^2$ metric was then calculated by comparing the imputed values to the known values.

FIG. 12A and FIG. 12B are graphs that illustrate example surprising good performance using the methods described herein compared to conventional and more costly methods, according to various embodiments. In each case the horizontal axis indicates allele frequency in the reference genome; and, the vertical axis indicates the $r^2$ metric when the imputed genotype is compared to the truth. In FIG. 12A the $r^2$ metric is plotted for the two genotyping methods (Illumina GSA, trace 1211 and Illumina CoreExome, trace 1212) and the two sequencing approaches (0.4×, trace 1213, and 0.2×, trace 1214) when applied in a European population. The sequencing approach at 0.2× (trace 1214) coverage is nearly equivalent to the array performance (trace 1211), and surprisingly, the sequencing approach at 0.4× coverage (trace 1213) outperforms the arrays (trace 1211 and trace 1212). In FIG. 12B, these same metrics are shown for an African population, the two genotyping methods (Illumina GSA, trace 1221 and Illumina CoreExome, trace 1222) and the two sequencing approaches (0.4×, trace 1223, and 0.2×, trace 1224. In this population, it is remarkable that even 0.2× genome coverage (trace 1224) outperforms both arrays (trace 1221 and 1222). The surprising superior performance is likely because many genotyping arrays are optimized for European populations, while the random low coverage sequencing approaches described here have no such biases.

Computational Hardware Overview

FIG. 13 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1300, or a portion thereof, constitutes a means for performing one or more steps of one or more methods described herein.

A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitutes computer instructions.

Computer system 1300 also includes a memory 1304 coupled to bus 1310. The memory 1304, such as a random access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device 1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1370 sends and receives electrical, acoustic or electromagnetic signals, including infrared and optical signals, that carry information streams, such as digital data.

The term computer-readable medium is used herein to refer to any medium that participates in providing information to processor 1302, including instructions for execution. Such a medium may take many forms, including, but not limited to, non-volatile media, volatile media and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1302, except for carrier waves and other signals.

Logic encoded in one or more tangible media includes one or both of processor instructions on a computer-readable storage media and special purpose hardware, such as ASIC 1320.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received, or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

Figure 14:
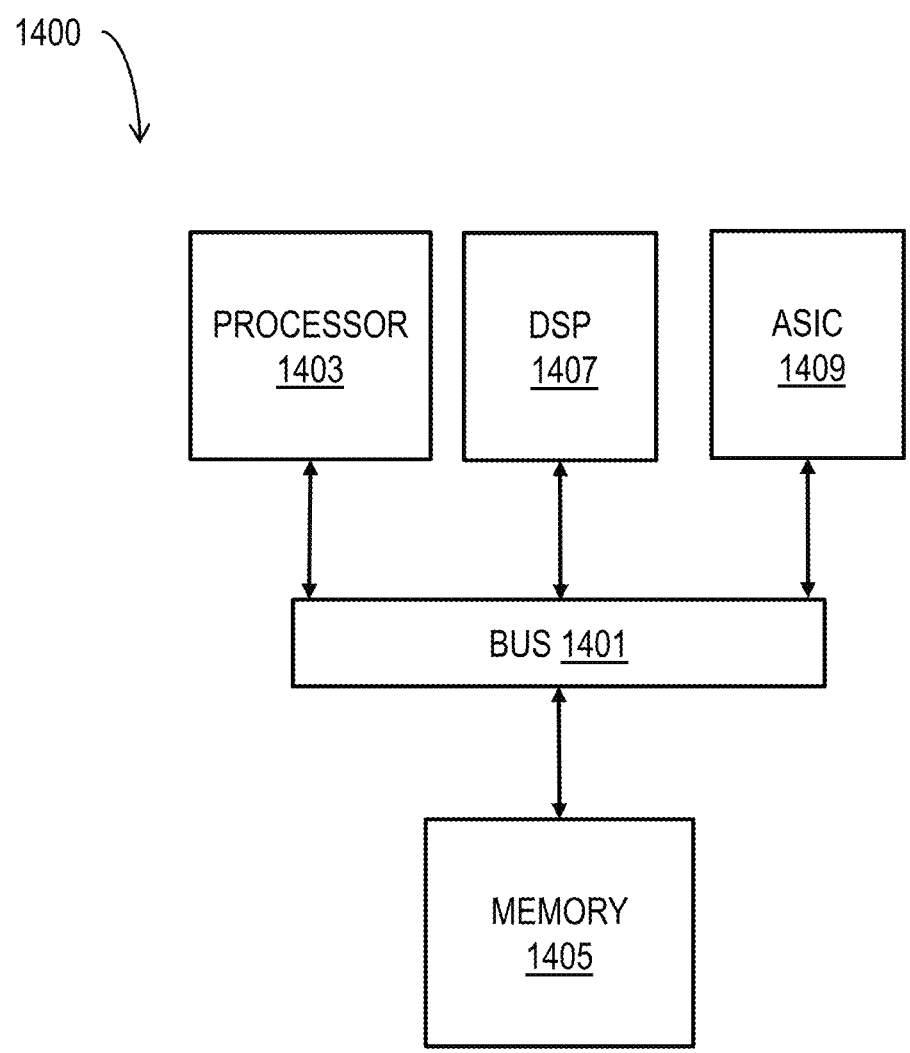
FIG. 14 illustrates a chip set upon which an embodiment of the invention may be implemented.

FIG. 14 illustrates a chip set 1400 upon which an embodiment of the invention may be implemented. Chip set 1400 is programmed to perform one or more steps of a method described herein and includes, for instance, the processor and memory components described with respect to FIG. 13 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1400, or a portion thereof, constitutes a means for performing one or more steps of a method described herein.

In one embodiment, the chip set 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1405 also stores the data associated with or generated by the execution of one or more steps of the methods described herein.

Figure 15:
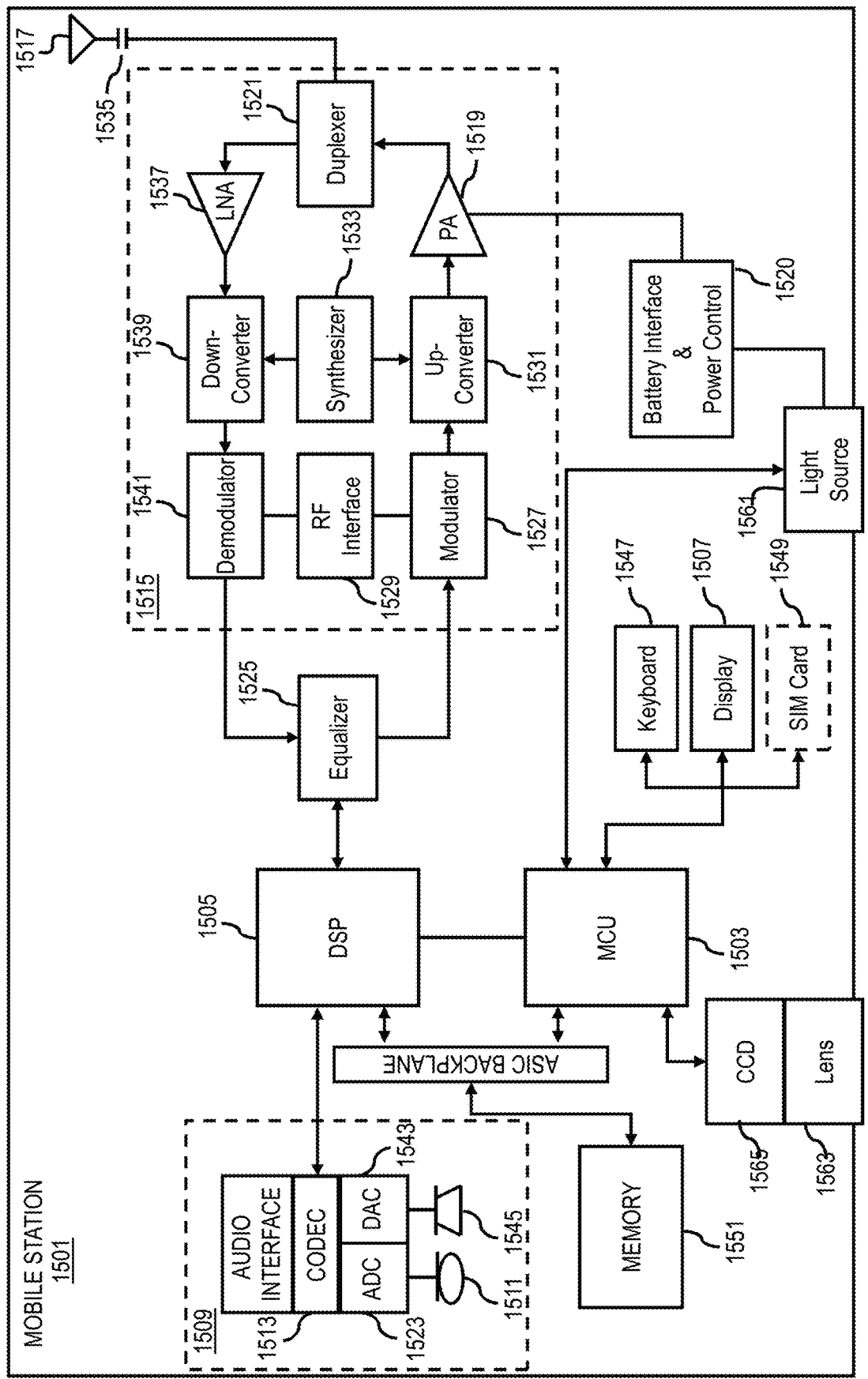
FIG. 15 is a diagram of exemplary components of a mobile terminal (e.g., cell phone handset) for communications, which is capable of operating in the system of 13, according to one embodiment.

FIG. 15 is a diagram of exemplary components of a mobile terminal 1500 (e.g., cell phone handset) for communications, which is capable of operating in the system of FIG. 2C, according to one embodiment. In some embodiments, mobile terminal 1501, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1503, a Digital Signal Processor (DSP) 1505, and a receiver/transmitter unit including a microphone gain control unit and a speaker gain control unit. A main display unit 1507 provides a display to the user in support of various applications and mobile terminal functions that perform or support the steps as described herein. The display 1507 includes display circuitry configured to display at least a portion of a user interface of the mobile terminal (e.g., mobile telephone). Additionally, the display 1507 and display circuitry are configured to facilitate user control of at least some functions of the mobile terminal. An audio function circuitry 1509 includes a microphone 1511 and microphone amplifier that amplifies the speech signal output from the microphone 1511. The amplified speech signal output from the microphone 1511 is fed to a coder/decoder (CODEC) 1513.

A radio section 1515 amplifies power and converts frequency in order to communicate with a base station, which is included in a mobile communication system, via antenna 1517. The power amplifier (PA) 1519 and the transmitter/modulation circuitry are operationally responsive to the MCU 1503, with an output from the PA 1519 coupled to the duplexer 1521 or circulator or antenna switch, as known in the art. The PA 1519 also couples to a battery interface and power control unit 1520.

In use, a user of mobile terminal 1501 speaks into the microphone 1511 and his or her voice along with any detected background noise is converted into an analog voltage. The analog voltage is then converted into a digital signal through the Analog to Digital Converter (ADC) 1523. The control unit 1503 routes the digital signal into the DSP 1505 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1525 for compensation of any frequency-dependent impairments that occur during transmission though the air such as phase and amplitude distortion. After equalizing the bit stream, the modulator 1527 combines the signal with a RF signal generated in the RF interface 1529. The modulator 1527 generates a sine wave by way of frequency or phase modulation. In order to prepare the signal for transmission, an up-converter 1531 combines the sine wave output from the modulator 1527 with another sine wave generated by a synthesizer 1533 to achieve the desired frequency of transmission. The signal is then sent through a PA 1519 to increase the signal to an appropriate power level. In practical systems, the PA 1519 acts as a variable gain amplifier whose gain is controlled by the DSP 1505 from information received from a network base station. The signal is then filtered within the duplexer 1521 and optionally sent to an antenna coupler 1535 to match impedances to provide maximum power transfer. Finally, the signal is transmitted via antenna 1517 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 1501 are received via antenna 1517 and immediately amplified by a low noise amplifier (LNA) 1537. A down-converter 1539 lowers the carrier frequency while the demodulator 1541 strips away the RF leaving only a digital bit stream. The signal then goes through the equalizer 1525 and is processed by the DSP 1505. A Digital to Analog Converter (DAC) 1543 converts the signal and the resulting output is transmitted to the user through the speaker 1545, all under control of a Main Control Unit (MCU) 1503 which can be implemented as a Central Processing Unit (CPU) (not shown).

The MCU 1503 receives various signals including input signals from the keyboard 1547. The keyboard 1547 and/or the MCU 1503 in combination with other user input components (e.g., the microphone 1511) comprise a user interface circuitry for managing user input. The MCU 1503 runs a user interface software to facilitate user control of at least some functions of the mobile terminal 1501 as described herein. The MCU 1503 also delivers a display command and a switch command to the display 1507 and to the speech output switching controller, respectively. Further, the MCU 1503 exchanges information with the DSP 1505 and can access an optionally incorporated SIM card 1549 and a memory 1551. In addition, the MCU 1503 executes various control functions required of the terminal. The DSP 1505 may, depending upon the implementation, perform any of a variety of conventional digital processing functions on the voice signals. Additionally, DSP 1505 determines the background noise level of the local environment from the signals detected by microphone 1511 and sets the gain of microphone 1511 to a level selected to compensate for the natural tendency of the user of the mobile terminal 1501.

The CODEC 1513 includes the ADC 1523 and DAC 1543. The memory 1551 stores various data including call incoming tone data and is capable of storing other data including music data received via, e.g., the global Internet. The software module could reside in RAM memory, flash memory, registers, or any other form of writable storage medium known in the art. The memory device 1551 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1549 carries, for instance, important information, such as the cellular phone number, the carrier supplying service, subscription details, and security information. The SIM card 1549 serves primarily to identify the mobile terminal 1501 on a radio network. The card 1549 also contains a memory for storing a personal telephone number registry, text messages, and user specific mobile terminal settings.

In some embodiments, the mobile terminal 1501 includes a digital camera comprising an array of optical detectors, such as charge coupled device (CCD) array 1565. The output of the array is image data that is transferred to the MCU for further processing or storage in the memory 1551 or both. In the illustrated embodiment, the light impinges on the optical array through a lens 1563, such as a pin-hole lens or a material lens made of an optical grade glass or plastic material. In the illustrated embodiment, the mobile terminal 1501 includes a light source 1561, such as a LED to illuminate a subject for capture by the optical array, e.g., CCD 1565. The light source is powered by the battery interface and power control module 1520 and controlled by the MCU 1503 based on instructions stored or loaded into the MCU 1503.

While the present disclosure has been discussed in terms of certain embodiments, it should be appreciated that the present disclosure is not so limited. The embodiments are explained herein by way of example, and there are numerous modifications, variations and other embodiments that can be employed that would still be within the scope of the present disclosure.

REFERENCES

All references cited herein are hereby incorporated by reference in their entirety.

1. Adey, et al., "Rapid, low-input, low-bias construction of shotgun fragment libraries by high-density in vitro transposition," Genome Biology, 2010, 11:R119.
2. Baym, et al., "Inexpensive multiplexed library preparation for megabase-sized genomes," PLosOne, 2015, 10(5).
3. Browning, et al., "Simultaneous genotype calling and haplotype phasing improves genotype accuracy and reduces false-positive associations for genome-wide association studies, Am J Hum Genet., 2009, 85(6):847-61.
4. Cai, et al., "Sparse whole-genome sequencing identifies two loci for major depressive disorder," Nature, 2015, 523, 588-591.
5. Green, et al., Molecular Cloning A Laboratory Manual, Volume I, Fourth Edition, Cold Spring Harbor Laboratory Press, 2012.
6. Hawkins, et al. Nucleic Acids Res., 1995; 23:22.
7. Kent, et al., "The human genome browser at UCSC," Genome Res., 2002, 12(6):996-1006.
8. Pasaniuc, et al., "Extremely low-coverage sequencing and imputation increases power for genome-wide association studies," Nature Genetics, 2012, 44(6), 631-635.
9. Picelli, et al., "Tn5 transposase and tagmentation procedures for massively scaled sequencing projects," Genome Research, 2016, 24:2033-2040.
10. Price, et al., "Principal components analysis corrects for stratification in genome-wide association studies," Nature Genetics, 2006, 38, 904-909.
11. Sullivan, P, "Genetics of disease: Associations with depression," Nature, 2015, 523, 539-540.
12. Skoglund, et al., "Origins and genetic legacy of Neolithic farmers and hunter-gatherers in Europe," Science, 2012, 336, 466-469.
13. Wang, et al., "Ancestry estimation and control of population stratification for sequence-based association studies," Nature Genetics, 46(4), 409-415.
14. Wood, et al., "Kraken: ultrafast metagenomic sequence classification using exact alignments," Genome Biology, 2014, 15:R46.

The invention claimed is:

1. A method for measuring a condition of an individual, comprising:
   a. procuring one or more genetic samples comprising genetic material from one or more individuals having a genotype, wherein each genetic sample is associated with the individual from which it was procured, wherein the genetic material is substantially non-ancient genetic material;
   b. sequencing the genetic material from each of the one or more genetic samples using only non-targeted, ultra-low coverage DNA sequencing with coverage of 1x or less relative to a first genome, to determine a plurality of genetic reads for each of the one or more genetic samples;
   c. aligning the plurality of genetic reads for each of the one or more genetic samples to one or more reference genomes, which can be the same as or different from the first genome, to produce a plurality of aligned genetic reads for each of the one or more genetic samples;
   d. storing in a database a locus and a value of each allele in the aligned reads along with a unique identifier for the associated individual and any personal behavior or phenotype information provided for the associated individual and any ancestry information and any relatedness to other individuals in the database for the associated individual,
   e. determining likelihood for a condition of the associated individual without imputing the genotype of any missing alleles for the associated individual, wherein the condition includes one or more biome species, or any new phenotype or new ancestry or new relatedness or new behavior not provided for the associated individual, wherein the new phenotype or new ancestry or new relatedness or new behavior is determined based on the alleles in the aligned reads for the individual in the ultra-low sequencing data and ultra-low sequencing data in the database about second alleles in second aligned reads for a second individual with any second phenotype and any second ancestry and any second relatedness and any second behavior;
   f. presenting, on a display device, the condition of the associated individual; and,
   g. repeating steps a through e until the likelihood for the condition meets or exceeds a predetermined threshold.

2. The method of claim 1, wherein the one or more reference genomes comprises a human reference genome.

3. The method of claim 1, wherein non-targeted, ultra-low coverage sequencing is about 0.9x, 0.8x, 0.7x, 0.6x, 0.5x, 0.4x, 0.3x, 0.2x, 0.1x, 0.05x, 0.04x, 0.03x, 0.02x, 0.01x, 0.009x, 0.008x, 0.007x, 0.006x, 0.005x, 0.004x, 0.003x, 0.002x or 0.001x coverage of the first genome.

4. The method of claim 1, wherein non-targeted, ultra-low coverage sequencing is about 0.001x to 1x, 0.008x to 0.08x, 0.01x to 0.5x and 0.04x to 0.4x coverage of the first genome.

5. The method of claim 1, wherein the condition is an ancestral group.

6. The method of claim 1, wherein the condition is a disease risk group.

7. The method of claim 1, wherein the one or more allelic variants is a rare disease variant.

8. The method of claim 7, wherein the rare disease variant is not predetermined.

9. The method of claim 1, wherein the one or more reference genomes comprise one or more non-human reference genomes, and wherein the method further comprises removing the plurality of aligned genetic reads for a human reference genome and comparing the remaining genetic reads to one or more non-human reference genomes to identify a plurality of non-human genetic reads.

10. The method of claim 9, wherein the one or more non-human reference genomes are of bacterial, viral or food origin.

11. The method of claim 1, wherein at least about 5% of the genetic material associated with an individual is derived from the individual from which the genetic sample has been procured.

12. The method of claim 1, wherein the biological sample is a saliva sample.

13. The method of claim 12, wherein sequencing the genetic material further comprises carrying out isolation or fragmentation or amplification, or some combination, on the genetic material at low-volume.

14. The method of claim 1, wherein sequencing the genomic DNA further comprises preparing sequencing libraries of sequenceable materials at low-volume.

15. The method of claim 5, further comprising:
   a. automatically determining on a processor a first likelihood for each variant in the plurality of aligned reads based on the first genome and storing the first likelihood in the database;
   b. automatically determining on a processor a second likelihood for each variant based on a reference genome for a particular ancestry of a plurality of reference genomes for a corresponding plurality of ancestries and storing the second likelihood in the database; and c. automatically determining on a processor a fraction of each ancestry of the plurality of ancestries based on the first likelihood and the second likelihood for a plurality of variants in the plurality of aligned reads and storing the fraction of each ancestry in the database.

16. The method of claim 1, wherein determining relatedness to a different individual in the database further comprises:

a. automatically determining on a processor a first ancestry of the individual and second ancestry of the different individual based on data in the database;
   b. automatically determining on a processor a first value of a variant from the plurality of aligned reads for the individual and a second value of the variant from a plurality of aligned reads for the different individual based on data in the database;
   c. automatically determining on a processor likelihood that the first value matches the second value based on the first ancestry and the second ancestry and a level L of relatedness, for a plurality of values of L;
   d. automatically determining on a processor an observed match has occurred if the first value matches the second value; and
   e. automatically determining on a processor a particular relatedness level that maximizes likelihood of observed match for each of a plurality of variants found in both the aligned reads of the individual and the aligned reads of the different individual.

17. The method of claim 1, wherein presenting the condition on the display device further causes the associated individual to receive treatment based on the condition.

* * * * *